US011981639B2

(12) United States Patent
Falchi et al.

(10) Patent No.: US 11,981,639 B2
(45) Date of Patent: *May 14, 2024

(54) PROCESS FOR THE PREPARATION OF A PDE4 INHIBITOR

(71) Applicant: CHIESI FARMACEUTICI S.p.A., Parma (IT)

(72) Inventors: Alessandro Falchi, Parma (IT); Emilio Lutero, Parma (IT); Emanuele Ferrari, Parma (IT); Fausto Pivetti, Parma (IT); Rocco Bussolati, Parma (IT); Edoardo Mariani, Parma (IT); Orsola Vecchi, Parma (IT); Erhard Bappert, Parma (IT); Caterina Ventrici, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/738,630

(22) Filed: May 6, 2022

(65) Prior Publication Data

US 2022/0348545 A1 Nov. 3, 2022

Related U.S. Application Data

(62) Division of application No. 16/934,527, filed on Jul. 21, 2020, now Pat. No. 11,352,327, which is a division of application No. 16/391,952, filed on Apr. 23, 2019, now Pat. No. 10,759,761, which is a division of application No. 15/802,737, filed on Nov. 3, 2017, now Pat. No. 10,323,003, which is a division of application No. 15/217,468, filed on Jul. 22, 2016, now Pat. No. 9,890,122, which is a division of application No. 14/516,976, filed on Oct. 17, 2014, now Pat. No. 9,434,691.

(30) Foreign Application Priority Data

Oct. 22, 2013 (EP) .................................. 13189784

(51) Int. Cl.
    C07D 213/89 (2006.01)
    A61K 9/00 (2006.01)
    C07D 213/61 (2006.01)

(52) U.S. Cl.
    CPC ............ C07D 213/89 (2013.01); A61K 9/007 (2013.01); C07D 213/61 (2013.01); C07B 2200/13 (2013.01)

(58) Field of Classification Search
    CPC .......................... C07D 213/89; C07D 213/61
    See application file for complete search history.

(56) References Cited

U.S. PATENT DOCUMENTS

| | | | |
|---|---|---|---|
| 8,383,826 B2* | 2/2013 | Delcanale | C07D 213/79 |
| | | | 546/301 |
| 8,440,834 B2 | 5/2013 | Amari et al. | |
| 8,648,204 B2 | 2/2014 | Amari | |
| 8,859,778 B2 | 10/2014 | Amari | |
| 9,056,176 B2 | 6/2015 | Amari | |
| 9,265,768 B2 | 2/2016 | Armani | |
| 9,358,224 B2 | 6/2016 | Bonelli | |
| 9,434,691 B2 | 9/2016 | Falchi | |
| 9,890,122 B2 | 2/2018 | Falchi | |
| 10,323,003 B2 | 6/2019 | Falchi | |
| 10,759,761 B2 | 9/2020 | Falchi | |
| 11,352,327 B2* | 6/2022 | Falchi | C07D 213/89 |
| 2009/0048220 A1 | 2/2009 | Delcanale | |
| 2010/0035908 A1 | 2/2010 | Felding | |
| 2010/0204256 A1 | 8/2010 | Amari et al. | |
| 2012/0034172 A1 | 2/2012 | Bonelli | |
| 2013/0156865 A1 | 6/2013 | Bonati | |
| 2014/0155391 A1 | 6/2014 | Armani | |
| 2015/0104516 A1 | 4/2015 | Cafiero | |
| 2015/0111931 A1 | 4/2015 | Falchi | |
| 2015/0342936 A1 | 12/2015 | Cocconi | |
| 2021/0038575 A1* | 2/2021 | Villetti | A61K 31/443 |
| 2022/0218678 A1* | 7/2022 | Villetti | A61K 31/443 |

FOREIGN PATENT DOCUMENTS

| | | |
|---|---|---|
| CN | 102317262 A | 1/2012 |
| EA | 010198 B1 | 6/2008 |
| EA | 017530 B1 | 1/2013 |
| JP | 2012-516863 A | 7/2012 |
| JP | 2016-519348 A | 6/2016 |

(Continued)

OTHER PUBLICATIONS

Extended European Search Report in Application No. 13189784.5 dated Dec. 19, 2013.
Chemical Abstracts STN Registry Database record for RN 1243411-75-7, entered Sep. 28, 2010.
Armani; J. Med. Chem. 2014, 57, 793-816.
Boswell-Smith; International Journal of COPD 2007, 2. 121-129.
Beghe; Am J Respir Crit Care Med 2013, 188, 271-278.
Singh; Synthesis 1992 (7): 605-617. (Year: 1992).
Naud; Adv. Synth. Catal. 2006, 348. 47-50. (Year: 2006).
Yanagisawa et al.—"Process Development of the PDE4 Inhibitor K-34", Organic Process Research & Development, ACS Publications, 2011, 15, pp. 376-381.

(Continued)

*Primary Examiner* — Daniel R Carcanague
(74) *Attorney, Agent, or Firm* — Oblon, McClelland, Maier & Neustadt, L.L.P.

(57) ABSTRACT

The present invention relates to a process for the preparation of compounds endowed with phosphodiesterase (PDE4) inhibitory activity having formula (I). The invention also relates to the process for the isolation by crystallization of the compound (I) and to its use for the preparation of pharmaceutical compositions for inhalation in combination with suitable carriers or vehicles. The present invention also relates to solvates and crystal forms of a compound of formula (I). The synthesized product is suitable for use in pharmaceutical applications for instance in the treatment of respiratory diseases.

20 Claims, 7 Drawing Sheets

(56) References Cited

FOREIGN PATENT DOCUMENTS

| WO | 2009018909 A2 | 2/2009 |
|---|---|---|
| WO | 2010/089107 | 8/2010 |
| WO | WO 2010/089107 A1 | 8/2010 |
| WO | WO 2011/157387 A1 | 12/2011 |
| WO | WO 2012/016845 A2 | 2/2012 |
| WO | WO 2012/071336 A1 | 5/2012 |
| WO | WO 2015/059050 A1 | 4/2015 |
| WO | WO-2023117985 A1 * | 6/2023 |

OTHER PUBLICATIONS

Indian Office Action dated Feb. 27, 2019 in Indian Patent Application No. 201617013726 (with English translation), citing documents AX therein, 6 pages.
Indian Office Action dated Sep. 27, 2021 in Indian Patent Application No. 201918021704 (with English translation), citing documents AX and AY therein, 2 pages.
Mino R. Caira, "Crystalline Polymorphism of Organic Compounds" Topics in Current Chemistry, Springer, Berlin, DE., vol. 198, Jan. 1, 1998, pp. 163-208.
Sudha R. Vippagunta, et al., "Crystalline Solids" Advanced Drug Delivery Reviews, vol. 48, 2001, pp. 3-26.
Russian Office Action and Search Report dated Sep. 1, 2022 in Russian Patent Application No. 2019105858/04(011196) (with English language translation), citing documents 10-13 and 20-24 therein, 29 pages.
Russian Office Action dated Jan. 30, 2023 in Russian Patent Application No. 2019105858/04(011196) (with English language translation), citing documents 10-12, 22-23, and 25-26 therein, 21 pages.
Notification of Reason for Refusal dated Apr. 4, 2023 in Japanese Patent Application No. 2022-025240 (with English language translation), citing document 14 therein, 7 pages.
Joel Bernstein, Polymorphism in molecular crystals, Chapter 7.3.2, Clarendon Press, 2002, pp. 244-249.
Klaus Kümmerer, "Pharmaceuticals in the Environment," Annual Review of Environment and Resources, vol. 35, 2010, 22 pages.
Sherry L. Morissette, et al., "High-throughput crystallization: polymorphs, salts, co-crystals and solvates of pharmaceutical solids", Advanced Drug Delivery Reviews, vol. 56, 2004, pp. 275-300.
Lian Yu, "Amorphous pharmaceutical solids: preparation, characterization and stabilization," Advanced Drug Delivery Reviews, vol. 48, 2001, pp. 27-42.
Joshua O. Odingo, "Inhibitors of PDE4: a review of recent patent literature," Expert Opinion on Therapeutic Patents, vol. 15, No. 7, 2005, 16 pages.
Narayan Variankaval, et al., "From Form to Function: Crystallization of Active Pharmaceutical Ingredients," American Institute of Chemical Engineers, AlChE Journal, vol. 54, No. 7, Jul. 2008, pp. 1682-1688.
I.G. Smirnova, et al., "Chapter 11.2. Interconnection of crystal structure of a substance, pharmacokinetic and efficacy of a medicament," Clinical pharmacokinetic: theoretical, applied and analytical aspects: guidelines, 2009, 8 pages.
IL office action dated Aug. 31, 2022, in corresponding Israel Patent Application No. 285528, 7 pages.
IL office action dated Aug. 28, 2022, in corresponding Israel Patent Application No. 285532, 5 pages.
IL office action dated Aug. 10, 2023, in corresponding Israel Patent Application No. 285528, 7 pages.
English translation of JP office action dated Jan. 25, 2023, in corresponding Japanese Patent Application No. 2022-025300 (with English translation), 4 pages.
English translation of AR office action dated Feb. 17, 2023, in corresponding Argentina Patent Application No. P200100438, 2 pages.
English translation of CN office action dated Oct. 28, 2022, in corresponding Chinese Patent Application No. 201910622800, 9 pages.
IN office action received on Jun. 28, 2022, in corresponding Indian Patent Application No. 202118050536, 6 pages.
METH-COHN. Otto. "A simple, powerful, and efficient method for transesterification." J. Chem. Soc., Chem. Commun., 1986. 9: 695-697.
Baumhof P et al. "A Mild and Effective Method for the Transesterification of Carboxylic Acid Esters". Angew. Chem. Int. Ed. 2001, 40, No. 19, pp. 3672-3674.
Caira Mr. "Crystalline polymorphism of organic compounds". Design of Organic Solids, vol. 198, pp. 163-208; Jan. 1, 1998.
Caira Mr, et al. "Structural relationships, thermal properties, and physicochemical characterization of anhydrous and solvated crystalline forms of tetroxoprim". Journal of Pharmaceutical Sciences, 2002, 91.2: 467-481.
Murphy NS, et al. "Solid-Phase Methodology for Synthesis of O-Alkylated Aromatic Oligoamide Inhibitors of alpha-Helix-Mediated Protein-Protein Interactions". Chem. Eur. J. Apr. 2, 20136; 19(18):5546-50.
Noriaki Hirayama, Organic Compound Crystal Preparation Handbook, 2008, pp. 17-23, 37-40, 45-51, 57-65.
Kazuhide Ashizawa, Salt/crystal shape Optimization and Crystallization Technology, Physico-Chemical Studies on the Molecular Details of Drug Crystals, Pharm Tech Japan, 2002, vol. 18, No. 10, pp. 81-96.
Experimental Science Course (continued) 2 Separation and Purification, Maruzen Co., Ltd., Jan. 25, 1967, pp. 159-162, 184-193.
Peng Song and Lin Hui, (Eds.). (2013) "Recrystallization." Organic Chemistry Experiments (pp. 69-74), Beijing: The Medicine Science and Technology Press of China.
3-Cyclopropyloxy-4-(methanesulfonamido)benzoic acid | C11H13NO5S—PubChem, <https://pubchem.ncbi.nlm.nih.gov/compound/72233209> Accessed Jan. 13, 2020, 7 pages.
Armani, E. et al., "Novel Class of Benzoic Acid Ester Derivatives as Potent PDE4 Inhibitors for Inhaled Administration in the Treatment of Respiratory Diseases," J. Med. Chem. 2014, 57, pp. 793-816.

* cited by examiner

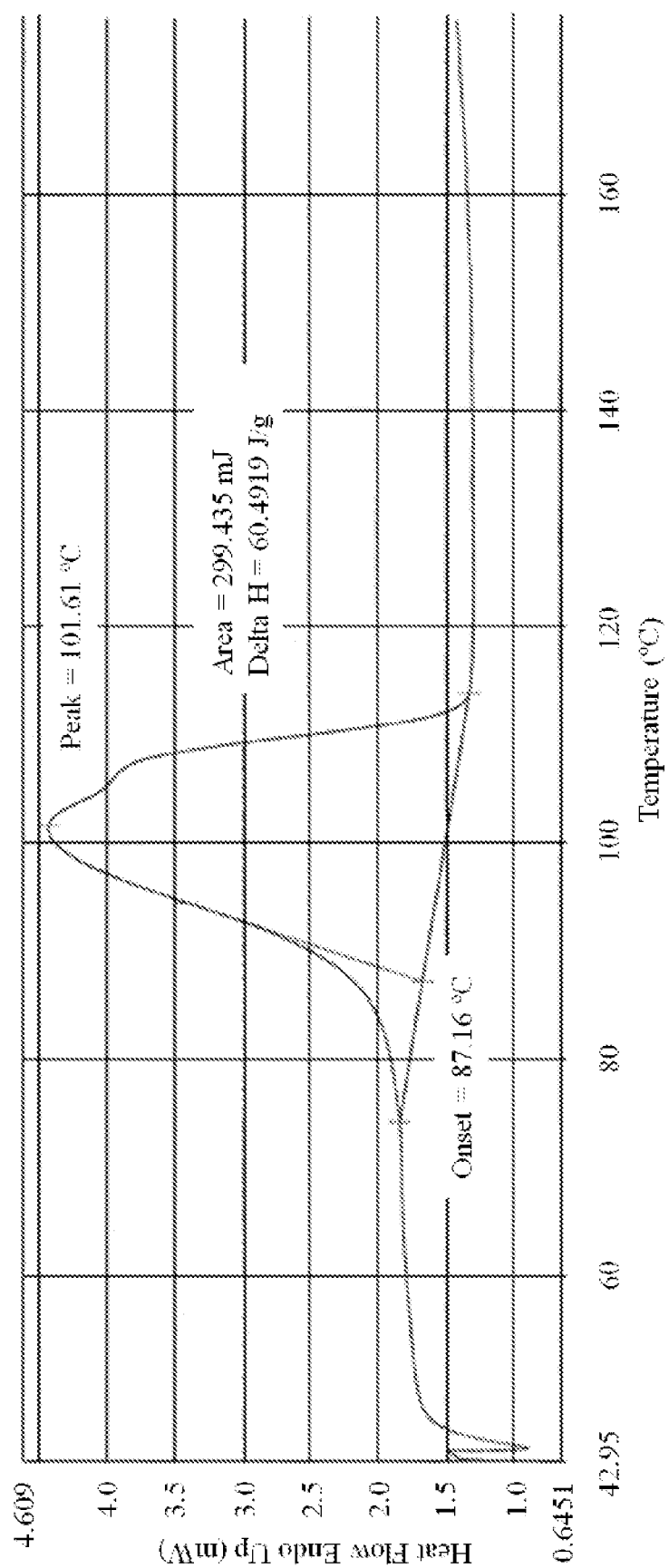

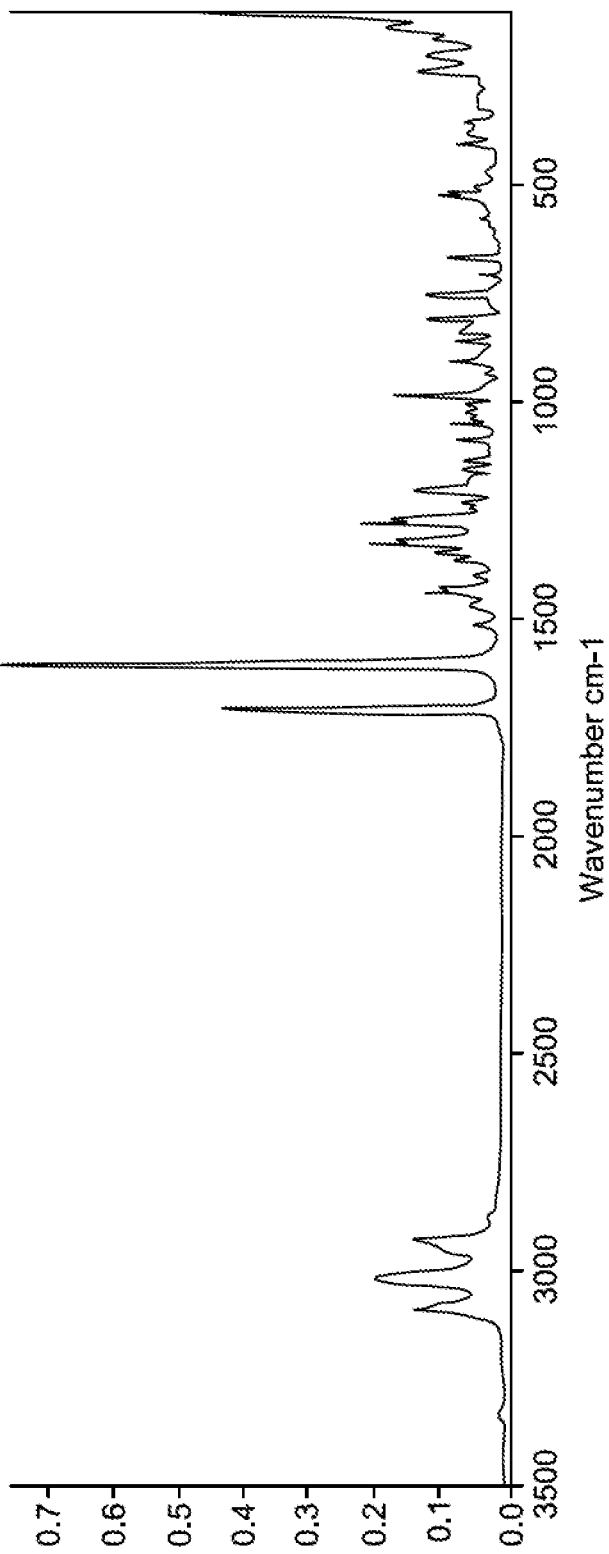
Fig. 2 – Raman spectrum of Compound (I), n=1 EtOH solvate

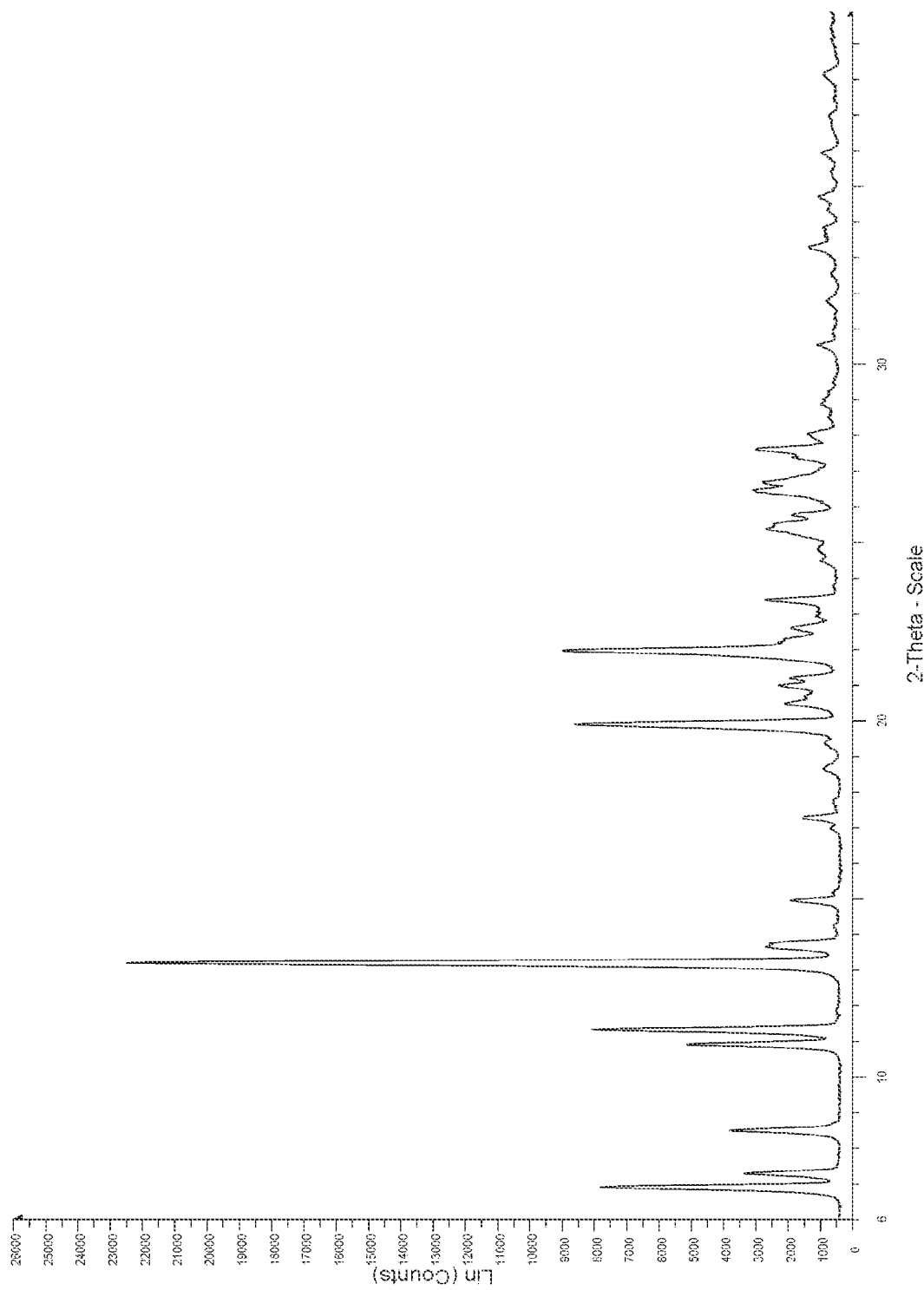

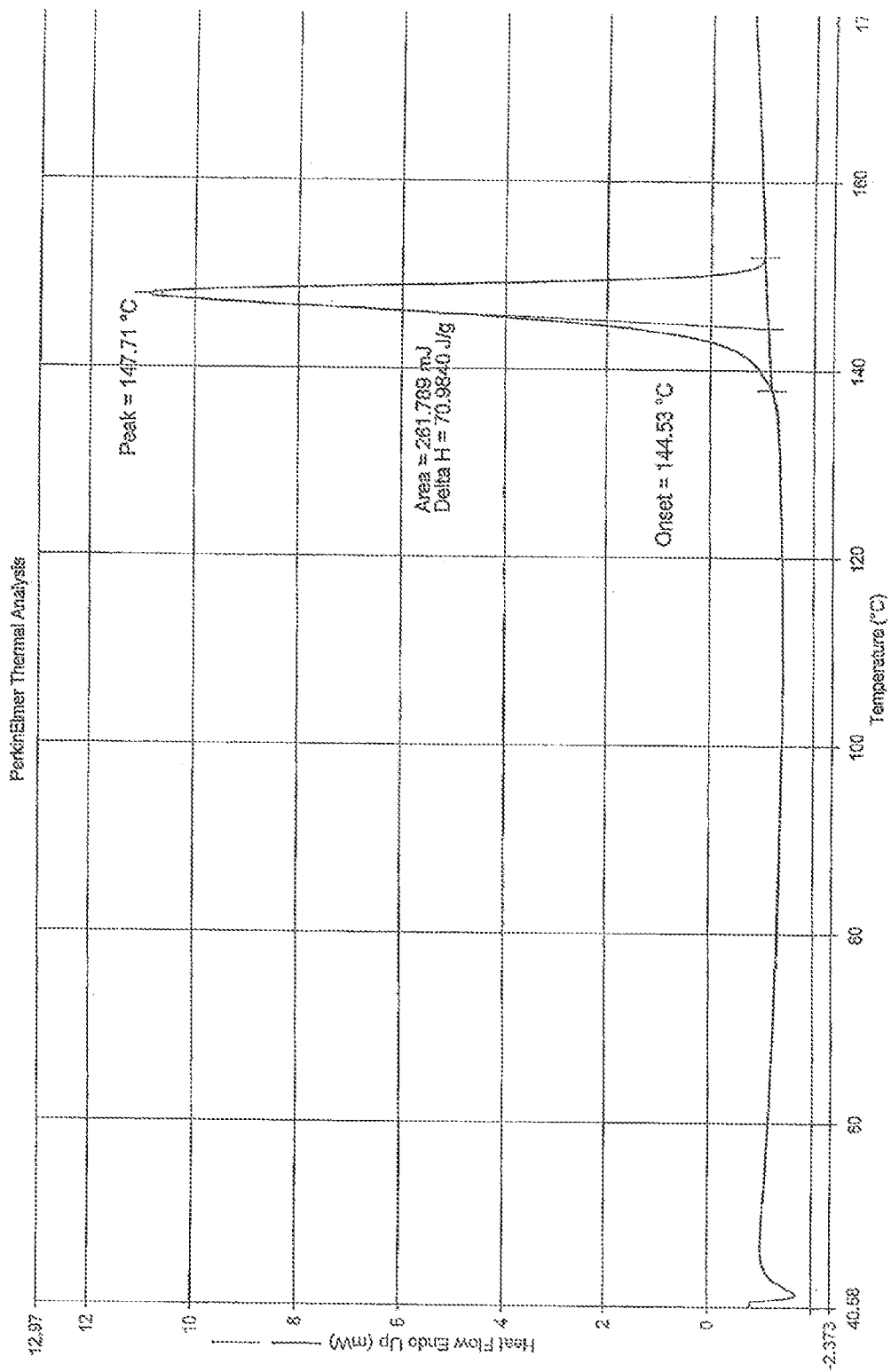
Fig. 4 - DSC of Compound (I), n=1 Form A from ethyl acetate/n-heptane

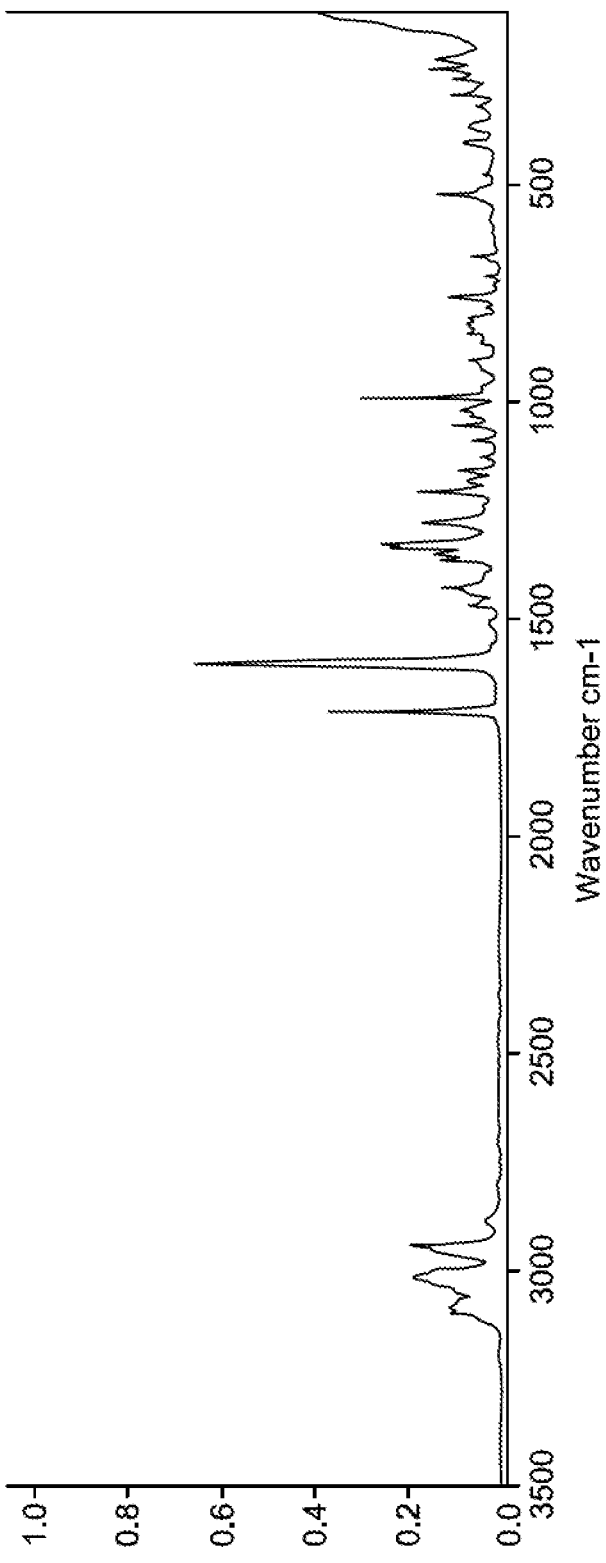

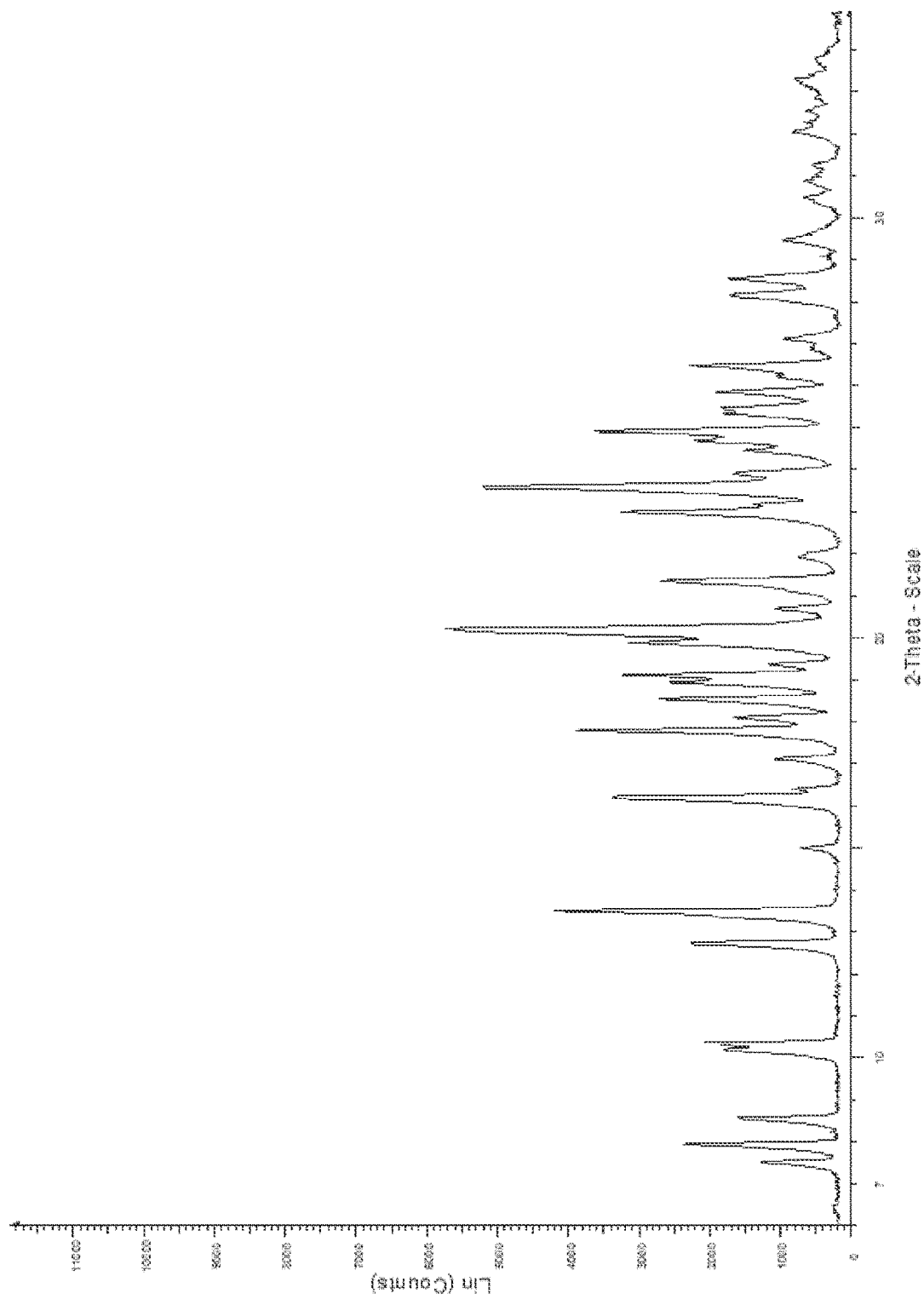
Fig. 6 - XRPD spectrum of Compound (I), n=1 Form A from ethyl acetate/n-heptane

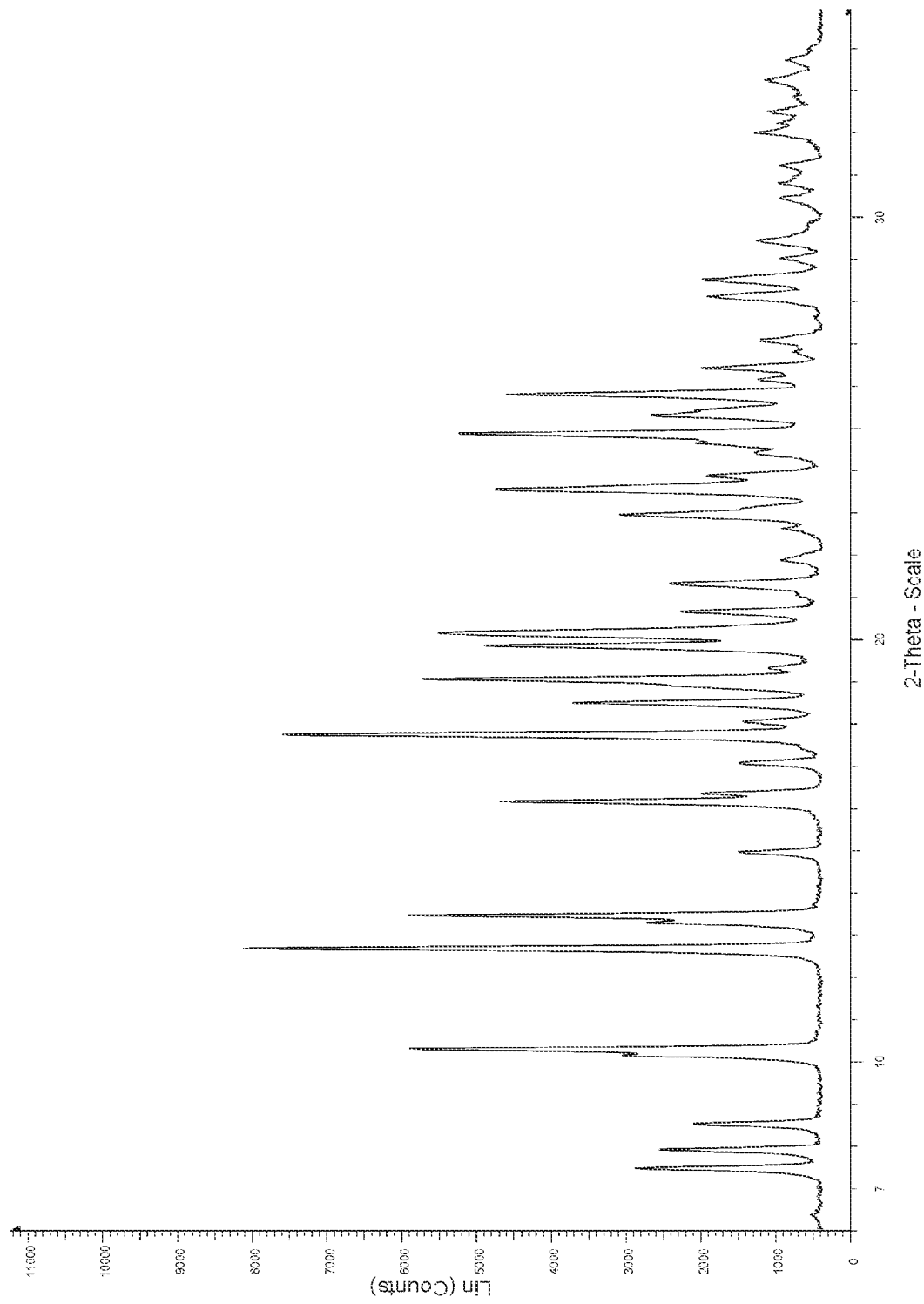
Fig. 7 - XRPD spectrum of Compound (I), n=1 Form A from isopropyl acetate

PROCESS FOR THE PREPARATION OF A PDE4 INHIBITOR

CROSS REFERENCES TO RELATED APPLICATIONS

This application is a divisional application of U.S. patent application Ser. No. 16/934,527, filed on Jul. 21, 2020, which was a divisional application of U.S. patent application Ser. No. 16/391,952, filed on Apr. 23, 2019 now U.S. Pat. No. 10,759,761, which was a divisional application of U.S. patent application Ser. No. 15/802,737, filed on Nov. 3, 2017, now U.S. Pat. No. 10,323,003, which was a divisional application of U.S. patent application Ser. No. 15/217,468, filed on Jul. 22, 2016, now U.S. Pat. No. 9,890,122, which was a divisional application of U.S. patent application Ser. No. 14/516,976, filed on Oct. 17, 2014, now U.S. Pat. No. 9,434,691, which claims priority to European Patent Application No. 13189784.5 filed on Oct. 22, 2013, which is incorporated herein by reference in its entirety.

BACKGROUND OF THE INVENTION

Field of the Invention

The present invention relates to processes for the preparation of compounds endowed with phosphodiesterase (PDE4) inhibitory activity. The present invention also relates to processes for the isolation by crystallization of such a compound and to its use for the preparation of pharmaceutical compositions for inhalation in combination with suitable carriers or vehicles. The present invention also relates to solvates and crystal forms of such a compound. The synthesized product is suitable for use in pharmaceutical applications for instance in the treatment of respiratory diseases.

Discussion of the Background

Compounds of formula (I) wherein n is 0 or 1:

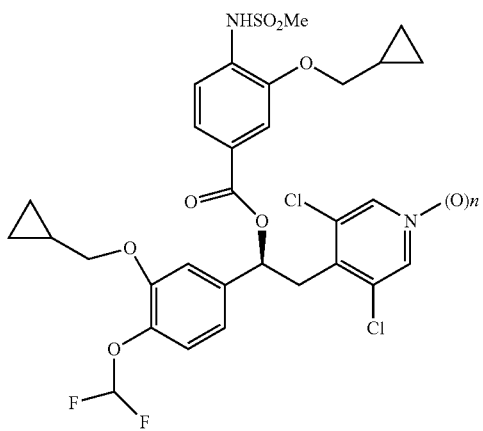

with chemical names (S)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester and (S)-3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester, obtained according to the invention, may be used for prophylactic purposes or for symptomatic relief for a wide range of conditions including respiratory disorders such as chronic bronchitis, chronic obstructive pulmonary disease (COPD), asthma of all types and allergic disease states such as atopic dermatitis and allergic rhinitis. Said compounds are disclosed in WO 2010/089107, which is incorporated herein by reference in it is entirety, as potent PDE4 inhibitors having excellent LPDE4 selectivity.

Processes for the preparation of compounds of formula (I) wherein n is 0 or 1 and analogues thereof, were also disclosed in WO 2010/089107, which is incorporated herein by reference in it is entirety.

Thus, there remains a need for improved processes for the preparation of such compounds.

SUMMARY OF THE INVENTION

Accordingly, it is one object of the present invention to provide novel processes for the preparation of compounds of formula (I).

This and other objects, which will become apparent during the following detailed description, have been achieved by the inventors' discovery of processes for the preparation of compounds of formula (I).

In particular, the present invention provides processes for the preparation of the compounds of formula (I) wherein n is 0 or 1 and the chiral carbon atom marked with an asterisk in the formula below has the (S) configuration.

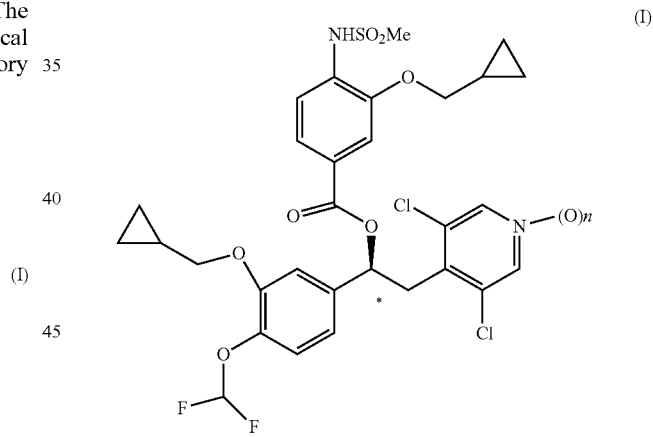

Said compounds are therapeutically useful because of their action as PDE4 inhibitors, so that related pharmaceutical compositions comprising them may be used in the prevention and treatment of respiratory diseases such as COPD (chronic bronchitis and emphysema), asthma, allergic rhinitis and atopic dermatitis; allergic disease states, inflammatory arthritis; Crohn's disease; reperfusion injury of the myocardium and brain; cystic fibrosis, arterial restenosis, atherosclerosis, keratosis, rheumatoid spondylitis, osteoarthritis, pyresis, diabetes mellitus, pneumoconiosis, toxic and allergic contact eczema; systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune disease; neurological and psychiatric disorders; stroke and spinal cord injury.

The invention relates to a particularly efficient process for the preparation of the compounds of formula (I) alternative to the one disclosed in the above cited prior art document.

This method is particularly advantageous in comparison with the known one because it provides for a simpler and safer procedure, with improved control of the process parameters and reproducibility, reduced number of synthesis steps and intermediate isolation, higher atom efficiency, reduced amounts of solvents, higher yields of products formation, and reduced impurities.

This method is also particularly suitable for industrial scale manufacturing.

A thermodynamically stable crystal form of the compound of formula (I) wherein n is 1, which will be hereinafter referred to as Form A, characterized by a high level of chemical purity and crystallinity as well as good handling qualities for pharmaceutical use, may be obtained according to the process of the present invention.

Crystal Form A of the present invention, for which its characteristic peaks in the X-ray powder diffraction (XRPD) pattern and melting range are given, may be selectively produced through crystallization by using appropriate solvents and operative conditions, as per the following detailed section.

Accordingly, the present invention also provides processes for the preparation of said Crystal Form A, comprising crystallization or re-crystallization under selected conditions.

As the said Crystal Form A may be used for prophylactic or therapeutic purposes, the present invention further provides the use of Crystal Form A of the compound of formula (I) wherein n is 1 in the manufacture of a medicament for the prevention and/or treatment of an inflammatory or obstructive respiratory disease such as asthma or chronic obstructive pulmonary disease (COPD).

In a still further aspect, the present invention provides a method of preventing and/or treating an inflammatory or obstructive respiratory disease such as asthma or chronic obstructive pulmonary disease (COPD), which comprises the inhalatory administration of an effective amount of crystal Form A.

Solvates of the compound of formula (I) wherein n is 1 are also obtained by operating with appropriate solvents.

Accordingly, the present invention also provides processes for the preparation of said solvates.

In particular, a solvate of a compound of formula (I) is obtained from ethanol and is distinguishable based upon its characteristic peaks in the X-ray powder diffraction (XRPD) pattern, and its characteristic melting range.

BRIEF DESCRIPTION OF THE DRAWINGS

A more complete appreciation of the present invention and many of the attendant advantages thereof will be readily obtained as the same become better understood by reference to the following detailed description when considered in connection with the accompanying drawings, wherein:

FIG. 1 is the differential scanning calorimetry (DSC) thermal trace of solvate from ethanol of the compound of formula (I) wherein n is 1.

FIG. 2 is the Raman spectrum of solvate from ethanol of the compound of formula (I) wherein n is 1.

FIG. 3 is the XRPD pattern of solvate from ethanol of the compound of formula (I) wherein n is 1.

FIG. 4 is the differential scanning calorimetry (DSC) thermal trace of the Crystalline Form A from ethyl acetate/n-heptane.

FIG. 5 is the Raman spectrum of the Crystalline Form A from ethyl acetate/n-heptane.

FIG. 6 is the XRPD pattern of the Crystalline Form A from ethyl acetate/n-heptane, recorded on a Bruker D8 Advance with Xray Diffraction Tube type KFL Cu 2k.

FIG. 7 is the XRPD pattern of the Crystalline Form A from isopropyl acetate.

DETAILED DESCRIPTION OF THE PREFERRED EMBODIMENTS

Unless defined otherwise, all technical and scientific terms used herein have the same meaning as it is commonly understood by one of ordinary skill in the art to which this subject matter belongs.

The term "high level of chemical purity" refers to a crystal form wherein the total amount of readily detectable impurities as determined by standard methods of analysis, such as thin layer chromatography (TLC) or high performance liquid chromatography (HPLC) is less than 5%, advantageously less than 2.5%, even less than 1.0%, or more preferably even less than 0.5% w/w.

The term "high level of crystallinity" refers to a crystal form wherein the percentage of crystallinity is equal to or higher than 90%, preferably higher than 95% w/w as determined by standard methods of analysis, such as X-ray powder diffraction or microcalorimetry.

The present invention provides a process for preparing a compound of formula (I):

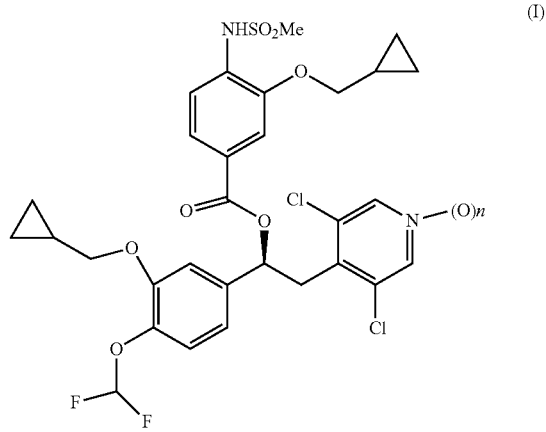

wherein n is 0 or 1, which process comprises:

(a) reacting a compound of formula (II):

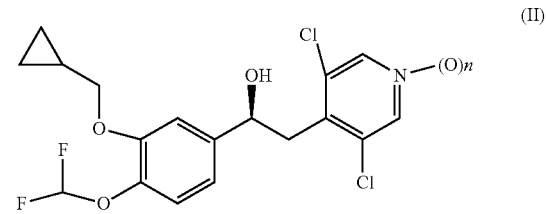

wherein n is 0 or 1, with a compound of formula (III):

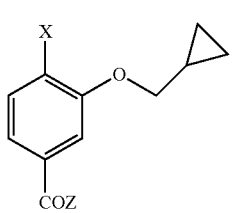
(III)

wherein X is selected from —NHSO$_2$Me and —NO$_2$ and Z is selected from —OH, chlorine, bromine, linear or branched (C$_1$-C$_6$)alkoxy, aryloxy, arylalkoxy, (C$_1$-C$_6$)alkylcarbonyloxy, arylcarbonyloxy, and aryl(C$_1$-C$_6$)alkylcarbonyloxy to obtain a compound of formula (I) wherein n is 0 or 1 or a compound of formula (IV):

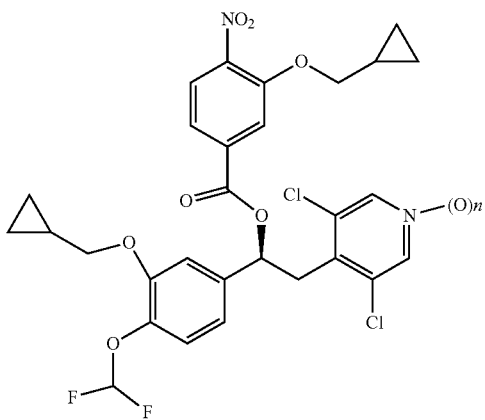
(IV)

wherein n has the above reported meanings; and, when a compound of formula (IV) is obtained in step (a):

(b) reducing it to a corresponding compound of formula (V):

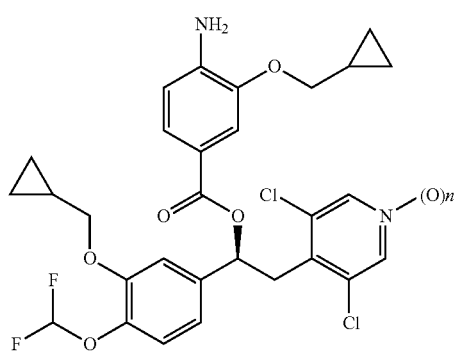
(V)

wherein n is 0 or 1, and reacting it with methanesulfonyl halide to obtain a compound of formula (I) wherein n has the above reported meanings;

and wherein the compound of formula (II) in step (a) is obtained according to any one of the alternative steps (c1) or (c2) or (c3) by:

(c1) oxidizing a compound of formula (VI):

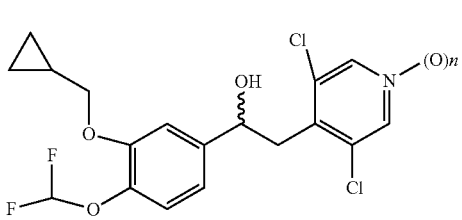
(VI)

wherein n is 0 or 1 to obtain a compound of formula (VII):

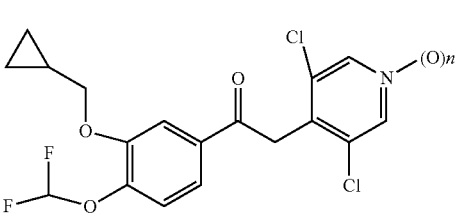
(VII)

wherein n is 0 or 1, and subsequently enantioselectively reducing it to obtain a compound of formula (II) wherein n has the above reported meanings; or (c2) chromatographically separating a compound of formula (VI) wherein n is 0 or 1, to obtain both a compound of formula (II) and a compound of formula (VIII):

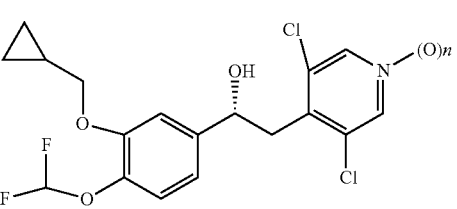
(VIII)

wherein n has the above reported meanings;

and optionally oxidizing the compound of formula (VIII) obtained in step (c2) to a corresponding compound of formula (VII) to be subsequently reduced to a compound of formula (VI) wherein n is 0 or 1 and reprocessed in the following chromatographic separation process; or (c3) reacting an intermediate of formula B":

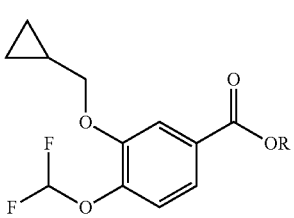
Intermediate B"

with an intermediate of formula D:

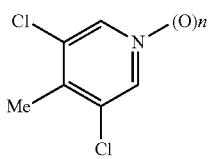

Intermediate D wherein R is a linear or branched (C₁-C₆) alkyl group or a arylalkyl group and n has the above reported meanings, to obtain directly a compound of formula (VII) and subsequently enantioselectively reducing it to obtain a compound of formula (II) wherein n has the above reported meanings;

and wherein all of the compounds of formula (I), (II), (IV), (V), (VI), (VII), or (VIII) wherein n is 1 can be obtained by oxidizing the corresponding compounds wherein n is 0.

In the present description, and unless otherwise provided, the bond with the symbol: 
in formula (VI) indicates a racemic mixture of the two enantiomers (R) and (S).

The bond with the symbol: 
in formulae (I) and (II) indicates the enantiomer (S), whereas the bond with the symbol: 
in formula (VIII) indicates the enantiomer (R).

The term linear or branched (C₁-C₆) alkyl group stands for a linear or branched alkyl group with from 1 to 6 carbon atoms, for example methyl, ethyl, n-propyl, isopropyl, n-butyl, isobutyl, sec-butyl, tert-butyl, n-pentyl, n-hexyl, and the like.

The term (C₁-C₆)arylalkyl refers to (C₁-C₆)alkyl groups further substituted by aryl.

The term linear or branched (C₁-C₆) alkoxy group means any alkyl-oxy chain wherein alkyl stands for a linear or branched alkyl group with from 1 to 6 carbon atoms, for example methoxy, ethoxy, n-propyloxy, isopropyloxy, n-butoxy, isobutoxy, sec-butoxy, tert-butoxy, n-pentyloxy, n-hexyloxy, and the like, preferably methoxy.

The term aryloxy group means any aryl group linked to the rest of the molecule through an oxygen atom, i.e. aryl-O-group. To this extent, and unless otherwise provided, aryl stands for an aromatic carbocyclic ring or aromatic heterocyclic ring, for instance comprising 5 or 6 membered rings with from 1 to 3 heteroatoms or heteroatomic groups selected from N, NH, O or S. The phenoxy group is preferred.

The term arylalkoxy means any (C₁-C₆)alkoxy substituted by one or more aryl groups, as defined above. Benzyloxy is preferred.

The term arylalkylcarbonyloxy means any (C₁-C₆)alkylcarbonyloxy substituted by one or more aryl groups, as defined above, preferably benzylcarbonyloxy.

The term halide, when referring to methanesulfonyl halide in step (b) of the process of the invention, means chloride and bromide.

In a preferred embodiment, the present invention provides a process for the preparation of a compound of formula (I) wherein n is 0 or 1, which process comprises reacting, in step (a), a compound of formula (II) wherein n has the above reported meanings with a compound of formula (III) wherein X is NHSO₂Me and Z has the above reported meanings.

According to an alternative preferred embodiment, the present invention provides a process for the preparation of a compound of formula (I) wherein n is 0 or 1, which process comprises reacting, in step (a), a compound of formula (II) wherein n has the above reported meanings with a compound of formula (III) wherein X is —NO₂ and Z has the above reported meanings.

According to a further preferred embodiment, the present invention provides a process for the preparation of a compound of formula (I) wherein n is 0 or 1, which process comprises reacting the compound of formula (II) being obtained as per step (c1), by oxidizing a compound of formula (VI) to a compound of formula (VII) and by enantioselectively reducing this latter to a compound of formula (II), wherein n has the above reported meanings.

According to a further preferred embodiment, the present invention provides a process for the preparation of a compound of formula (I) wherein n is 0 or 1, which process comprises reacting the compound of formula (II) obtained as per step (c2), by chromatographically separating a compound of formula (VI) to obtain both a compound of formula (II) and of formula (VIII), wherein n has the above reported meanings.

Even more preferably, according to this latter embodiment, the present invention provides a process for the preparation of a compound of formula (I) wherein n is 0 or 1, which process comprises reacting the compound of formula (II) obtained as per step (c2), by chromatographically separating a compound of formula (VI) to obtain both a compound of formula (II) and of formula (VIII), wherein n has the above reported meanings, and by then oxidizing the compound of formula (VIII) to a corresponding compound of formula (VII) to be subsequently reduced to a compound of formula (VI) that can be recycled in a further chromatographic separation.

According to a further preferred embodiment, the present invention provides a process for the preparation of a compound of formula (I) wherein n is 0 or 1, which process comprises reacting the compound of formula (II) obtained as per step (c3), reacting an intermediate of formula B":

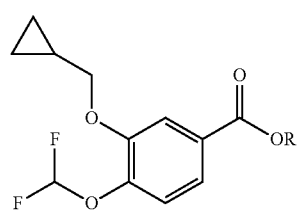

Intermediate B"

with an intermediate of formula D

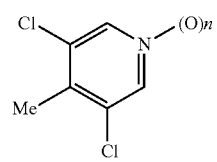

Intermediate D to obtain directly a compound of formula (VII) and subsequently enantioselectively reducing it to obtain a compound of formula (II) wherein n has the above reported meanings.

According to an additional preferred embodiment, the present invention provides a process for the preparation of a compound of formula (I) wherein n is 1, which process comprises oxidizing a compound of formula (I) wherein n is 0.

Alternatively, the present invention provides a process for the preparation of a compound of formula (I) wherein n is 1 by starting from a compound of formula (II) wherein n is 1, this latter having been obtained by oxidation of the corresponding compound of formula (II) wherein n is 0.

Alternatively, the present invention provides a process for the preparation of a compound of formula (I) wherein n is 1 by starting from a compound of formula (IV) wherein n is 1, this latter having been obtained by oxidation of the corresponding compound of formula (IV) wherein n is 0.

Alternatively, the present invention provides a process for the preparation of a compound of formula (I) wherein n is 1 by starting from a compound of formula (V) wherein n is 1, this latter having been obtained by oxidation of the corresponding compound of formula (V) wherein n is 0.

Alternatively, the present invention provides a process for the preparation of a compound of formula (I) wherein n is 1 by starting from a compound of formula (VI) wherein n is 1, this latter having been obtained by oxidation of the corresponding compound of formula (VI) wherein n is 0.

Alternatively, the present invention provides a process for the preparation of a compound of formula (I) wherein n is 1 by starting from a compound of formula (VII) wherein n is 1, this latter having been obtained by oxidation of the corresponding compound of formula (VII) wherein n is 0.

According to step (a) of the present invention, the process provides for the preparation of a compound of formula (I) or of formula (IV) by reacting a compound of formula (II) with a compound of formula (III) wherein n, X and Z have the above reported meanings.

More in particular, when the compound of formula (III) is used wherein Z is —OH, the reaction is carried out in the presence of a coupling reagent selected from DCC, CDI, HATU, HBTU, TBTU, DMTMM, COMU, EDCI, with or without HOBt, with or without an organic base like TEA, DIPEA, NMM, DBU, DBO, pyridine, and DMAP, in a solvent selected from dimethyl sulfoxide, sulfolane, dimethyl formamide, dimethyl acetamide, N-methyl pyrrolidone, toluene, benzene, xylene, acetone, isopropyl ketone, methyl ethyl ketone, methyl isobutyl ketone, THF, dioxane, 2-methoxyethyl ether, diethyl ether, isopropyl ether, t-butyl methyl ether, ethyl acetate, isopropyl acetate, acetonitrile, dichloromethane, chloroform, chlorobenzene, and mixtures thereof.

When the compound of formula (III) is an acyl chloride or bromide, or an activated ester or a mixed anhydride, the reaction is carried out as above described without the presence of a coupling reagent.

Preferably, the above reaction with a compound of formula (III) wherein X is —NHSO$_2$Me is conducted with CDI and DBU in ethyl acetate.

In an alternative preferred embodiment, when the reaction is carried out with a compound of formula (III) wherein X is —NO$_2$, so as to give rise to a compound of formula (IV), the above reaction is conducted with EDCI and DMAP in DMF.

According to step (b) of the process, to be optionally carried out when starting from a compound of formula (III) wherein X is —NO$_2$ in step (a), the compound of formula (IV) wherein n has the above reported meanings is first reduced to the corresponding amino derivative of formula (V) and then properly reacted with a methanesulfonyl halide to obtain the compound of formula (I).

Preferably, the reducing step is carried out with a reducing agent selected from hydrogen, cyclohexadiene, ammonium formate, formic acid, iron, tin dichloride, tin, nickel chloride, nickel, lithium aluminium hydride, sodium aluminium hydride, lithium borohydride, sodium borohydride, potassium borohydride, and sodium hydrosulfite.

In an even more preferred embodiment, when the reaction is carried out with hydrogen, cyclohexadiene, ammonium formate and formic acid, then the reaction is carried out in the presence of a catalyst selected from palladium- platinum- or nickel-based catalysts, or it is selected from the group consisting of palladium on carbon, palladium on barium sulphate and palladium on calcium carbonate.

In an even more preferred embodiment, when formic acid is used, the reaction is carried out in the presence of ammonia or an amine, preferably triethylamine.

Suitable solvents for the above reducing step are selected from water, methanol, ethanol, isopropanol, n-butanol, t-butanol, dimethyl formamide, dimethyl acetamide, N-methyl pyrrolidone, toluene, benzene, xylene, THF, dioxane, 2-methoxyethyl ether, diethyl ether, isopropyl ether, t-butyl methyl ether, ethyl acetate, isopropyl acetate, acetonitrile, and mixtures thereof.

More preferably, the reaction is carried out with hydrogen with palladium on charcoal in ethyl acetate.

The subsequent reaction of the compound of formula (V) with methanesulfonyl halide is carried out in the presence of suitable solvents such as toluene, benzene, xylene, tetrahydrofuran, dioxane, 2-methoxyethyl ether, diethyl ether, isopropyl ether, t-butylmethyl ether, ethyl acetate, isopropyl acetate, acetonitrile, dichloromethane, chloroform, chlorobenzene, and mixtures thereof and a base preferably selected from sodium hydroxide, sodium carbonate, sodium bicarbonate, sodium hydride, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethyl-amine), NMM (N-Methylmorpholine), DBU (1,8-Diazabicyclo[5.4.0]undec-7-ene), DBO (1,4-Diazabicyclo[2.2.2]octane), pyridine, and DMAP (4-dimethylaminopyridine); in the case when pyridine is used in excess other solvents can be avoided.

Preferably, the reaction is carried out with triethylamine in dichloromethane.

According to step (c1) for the preparation of the compound of formula (II), the compound of formula (VI) is first oxidized to the corresponding keto derivative of formula (VII) which is then enantioselectively reduced to the compound of formula (II).

Oxidation is preferably carried out in the presence of an oxidizing agent selected from a metallic oxide such as MnO$_2$, a hypervalent iodine, like 2-Iodoxybenzoic acid (IBX) or Dess-Martin periodinane, dimethylsulfoxide-based oxidants (Swern) like sulfur trioxide pyridine complex, in a solvent selected from water, dimethyl formamide, dimethyl acetamide, N-methyl pyrrolidone, dimethyl sulfoxide, sulfolane, toluene, benzene, xylene, acetone, isopropyl ketone, methyl ethyl ketone, methyl isobutyl ketone, ethyl acetate, isopropyl acetate, acetonitrile, dichloromethane, THF, dioxane, and mixtures thereof.

Even more preferably the reaction is carried out with MnO$_2$ in toluene or with a Swern oxidant in DMSO.

Compound of formula (VI) can be prepared from intermediate of formula B:

Intermediate B

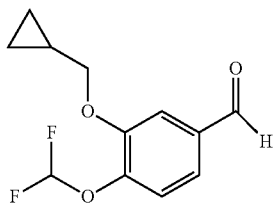

and intermediate of formula D wherein n=0

Intermediate D

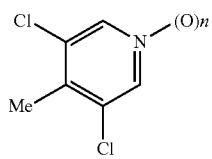

as described in WO 2010/089107, which is incorporated herein by reference in its entirety.

According to step (c3) for the preparation of the compound of formula (II), the intermediate of formula B':

Intermediate B'

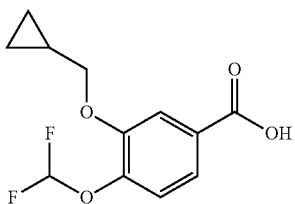

is converted to intermediate of formula B":

Intermediate B"

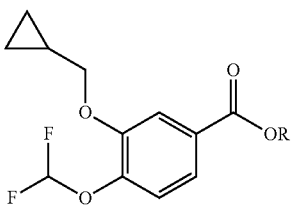

by reaction with thionyl chloride, hydrogen chloride, sulfuric acid in methanol, ethanol, isopropanol, n-butanol, t-butanol, benzyl alcohol with or without other solvents, or by reaction with the relative alkyl halide in the presence of suitable solvents such as methanol, ethanol, isopropanol, n-butanol, t-butanol, dimethyl formamide, dimethyl acetamide, N-methyl pyrrolidone, tetrahydrofuran, dioxane, ethyl acetate, isopropyl acetate, acetonitrile, dichloromethane, and mixtures thereof and a base preferably selected from sodium hydroxide, sodium carbonate, sodium bicarbonate, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethyl-amine), NMM (N-Methylmorpholine), pyridine.

More preferably, the above reaction is conducted with potassium carbonate in dimethyl formamide or dimethyl acetamide.

Intermediate B' can be obtained by oxidation of intermediate B with an oxidizing agent selected from hydrogen peroxide, an organic peracid, like paracetic acid, or m-chloroperbenzoic acid, or a mineral peracid like persolforic acid or Oxone® ($KHSO_5*½KHSO_4*½K_2SO_4$), in the presence of suitable solvents such as water, methanol, ethanol, isopropanol, n-butanol, t-butanol, dimethyl formamide, dimethyl acetamide, N-methyl pyrrolidone, tetrahydrofuran, dioxane, 2-methoxyethyl ether, isopropyl acetate, acetonitrile, and mixtures thereof. More preferably, the above reaction is conducted with Oxone® in methanol.

Alternatively intermediate B" can be prepared directly from intermediate B by oxidation with Oxone® in the corresponding alkyl alcohol as solvent.

Alternatively intermediate B" can be prepared from conversion of intermediate C' into intermediate C":

Intermediate C"

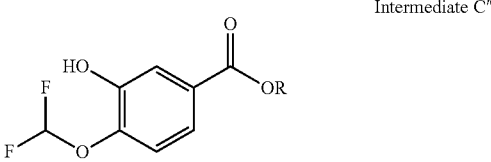

by Pinner reaction with sulfuric acid in the corresponding alkyl alcohol as solvent, followed by alkylation with cyclopropyl bromide in the presence of suitable solvents such as toluene, benzene, xylene, tetrahydrofuran, dioxane, 2-methoxyethyl ether, diethyl ether, isopropyl ether, t-butylmethyl ether, ethyl acetate, isopropyl acetate, acetonitrile, dichloromethane, chloroform, chlorobenzene, and mixtures thereof and a base preferably selected from sodium hydroxide, sodium carbonate, sodium bicarbonate, sodium hydride, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethyl-amine), NMM (N-Methylmorpholine), DBU (1,8-Diazabicyclo[5.4.0]undec-7-ene), DBO (1,4-Diazabicyclo[2.2.2]octane), pyridine, and DMAP (4-dimethylaminopyridine).

Intermediate B" is then converted to the corresponding keto derivative of formula (VII) by reaction with intermediate D in presence of a base preferably selected from lithium diisopropylamide (LDA), butyl lithium, hexyl lithium, pentyl lithium, lithium bis(trimethylsilyl)amide (LHMDS), sodium bis(trimethylsilyl)amide, and potassium t-butylate, in the presence of suitable solvents such as toluene, benzene, xylene, tetrahydrofuran, methyl-tetrahydrofuran, dioxane, 2-methoxyethyl ether, diethyl ether, isopropyl ether, t-butylmethyl ether, and mixtures thereof.

More preferably, the above reaction is conducted with LHMDS in THF.

The subsequent enantioselective reducing step is preferably carried out with a reducing agent selected from hydrogen in the presence of a heavy metal chiral complex preformed or formed in situ. In situ formation may occur by reacting a Ru-, Rh- or Ir-complex such as $RuCl_2(PPh_3)_3$, [Ru(p-cymene) $Cl_2]_2$, [$RhCI_2(CP^*)]_2$ or [$IrCI_2(Cp^*)]_2$ with a chiral ligand such as SL-N004-1 ((S)-4-tert-Butyl-2-[(S)-2-(bis(1-phenyl)phosphino)ferrocen-1-yl]oxazoline,),
SL-N003-1 ((R)-4-Isopropyl-2-[(R)-2-(diphenylphosphino)-ferrocen-1-yl]Oxazoline), (S, S)-$T_S$-DPEN ((1S,2S)-

(−)-N-p-tosyl-1,2-diphenylethylenediamine), (S,S)-Ms-DPEN ((1S,2S)-(−)-N-Mesyl-1,2-diphenylethylenediamine), (R)-DAIPEN ((2R)-(−)-1,1-Bis(4-methoxyphenyl)-3-methyl-1,2-butanediamine), or (1R,2S)-1-Amino-2-indanol.

The above reduction reaction is preferably carried out in the presence of a base, preferably selected from sodium hydroxide, sodium carbonate, sodium $C_1$-$C_4$ alcoholates, sodium bicarbonate, sodium hydride, potassium hydroxide, potassium carbonate, potassium $C_1$-$C_4$ alcoholates, potassium bicarbonate, lithium hydroxide, lithium carbonate, lithium $C_1$-$C_4$ alcoholates, caesium hydroxide, caesium carbonate, caesium bicarbonate, triethyl amine, pyridine, and 4-dimethylaminopyridine.

In an even more preferred embodiment, the reaction is carried out with the complex formed in situ by reacting $RuCl_2(PPh_3)_3$ and the chiral ligand SL-N004-1, in toluene and in the presence of aqueous sodium hydroxide.

Alternatively the compounds of formula (II) and (VIII) may be separated by preparative chiral chromatography; a batch procedure may be adopted loading the chiral column with a solution of racemic (VI) in several runs and collecting the eluted fractions of separated enantiomers. A simulated moving bed (SMB) procedure should be considered to separate large amounts of material.

Advantageously, according to an alternative embodiment of the present invention, once the compounds of formula (II) and (VIII) have been separated through preparative chiral HPLC techniques, the compound of formula (VIII) may be conveniently reconverted into the compound of formula (VI) through oxidation to the corresponding derivative of formula (VII) and subsequent reduction and reprocessed in the following chromatographic separation process, as formerly reported.

The reduction can be carried out with lithium aluminium hydride, sodium aluminium hydride, lithium borohydride, sodium borohydride, or potassium borohydride in a solvent like water, methanol, ethanol, isopropanol, n-butanol, t-butanol, toluene, benzene, xylene, THF, dioxane, 2-methoxyethyl ether, diethyl ether, isopropyl ether, t-butyl methyl ether, and mixtures thereof.

It should be understood that all of the compounds of the present invention wherein n is 0 can be transformed into corresponding compounds wherein n is 1 by oxidation with an oxidizing agent selected from hydrogen peroxide, an organic peracid, like paracetic acid, or m-chloroperbenzoic acid, or a mineral peracid like persolforic acid, or Oxone® ($KHSO_5$*½$KHSO_4$*½$K_2SO_4$), in a solvent selected from the group consisting of water, methanol, ethanol, isopropanol, n-butanol, t-butanol, dimethyl formamide, dimethyl acetamide, N-methyl pyrrolidone, toluene, benzene, xylene, acetone, isopropyl ketone, methyl ethyl ketone, methyl isobutyl ketone, THF, dioxane, ethyl acetate, isopropyl acetate, acetonitrile, acetic acid, and mixtures thereof.

More preferably, the above reaction is conducted on (I) or on (II) wherein n is 0 with Oxone® in water and methanol.

From all of the above, it is clear that when preparing the compounds of formula (I) according to any one of the aforementioned process variants, optional functional groups within the starting materials or the intermediates thereof and which could give rise to unwanted side reactions, need to be properly protected according to conventional techniques. Likewise, the conversion of these latter into the free deprotected compounds may be carried out according to known procedures.

The intermediate compounds of formula (IV) and (V) and wherein n is 0 or 1 are novel and, hence, represent a further embodiment of the present invention.

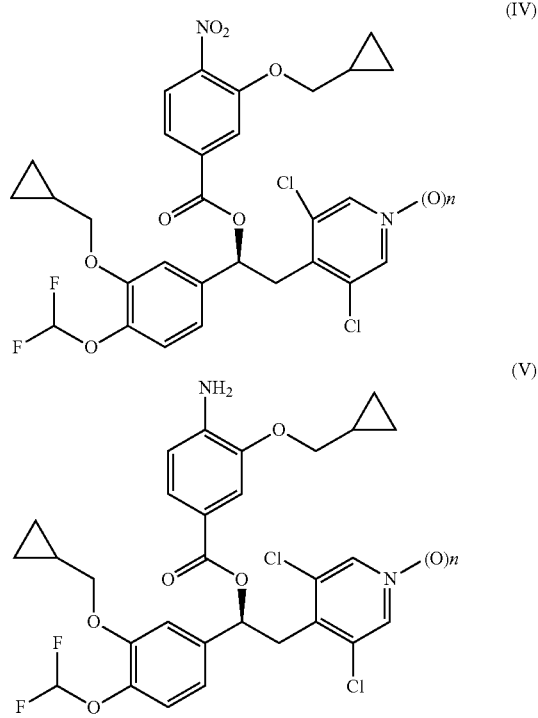

The compounds of formula (VI), as starting materials of the present process, are known or can be prepared according to known methods.

As an example, the compounds of formula (VI) and their preparation are disclosed in WO 2010/089107, which is incorporated herein by reference in its entirety.

Compound of formula (III) wherein X is —NHSO$_2$Me and Z is —OH represents a further embodiment of the present invention.

The other starting materials of formula (III) are known or readily prepared according to known methods.

As an additional example, the compounds of formula (III) wherein X is —NHSO$_2$Me can be prepared from the corresponding derivatives wherein X is —NO$_2$ by reduction of these latter to the amino derivatives and by their subsequent reaction with a methanesulfonyl halide, essentially as formerly described.

Likewise, the preparation of the compounds of formula (III) where Z is —OH can be obtained through conventional hydrolysis of the corresponding ester derivatives.

To this extent, the hydrolysis reaction for instance occurring on a compound of formula (III) wherein Z is methoxy can be easily accomplished in the presence of a suitable base selected from sodium hydroxide, sodium carbonate, potassium hydroxide, potassium carbonate, lithium hydroxide, lithium carbonate, caesium hydroxide, and caesium carbonate; the solvent being selected from water alone or in mixture with methanol, ethanol, isopropanol, n-butanol, t-butanol, dimethyl sulfoxide, sulfolane, toluene, benzene, xylene, THF, dioxane, and mixtures thereof.

More preferably, the hydrolysis reaction of the esters into the free acid wherein Z is —OH is carried out with NaOH in THF and water.

Likewise, the preparation of the compounds of formula (III) wherein Z is other than —OH can be accomplished according to well-known esterification or transesterification techniques or starting from the relative ester of the 3-hydroxy-4-nitrobenzoic acid.

The present invention also provides a process for the preparation of additional compounds of formula (IX) that, with respect to the above compounds of formula (I), bear additional $R_1$ and $R_2$ groups in place of the cyclopropylmethyl and difluoromethyl groups of formula (I).

Said compounds of formula (IX) may be used for prophylactic purposes or for symptomatic relief for a wide range of conditions including respiratory disorders such as chronic bronchitis, chronic obstructive pulmonary disease (COPD), asthma of all types and allergic disease states such as atopic dermatitis and allergic rhinitis.

Accordingly, the present invention also provides a process for the preparation of the compounds of formula (XI):

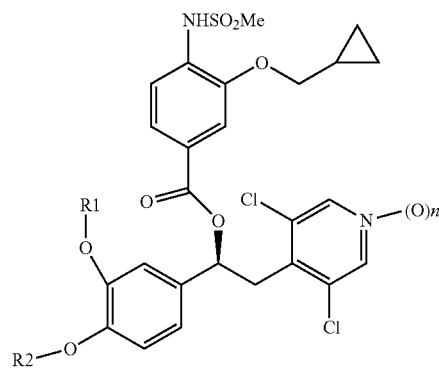

(XI)

wherein n is 0 or 1;

and $R_1$ and $R_2$, are independently selected in a group consisting of H, linear or branched $(C_1-C_6)$ alkyl, optionally substituted by one or more substituents selected from halogen atoms, $(C_3-C_7)$ cycloalkyl; $(C_5-C_7)$cycloalkenyl; linear or branched $(C_2-C_6)$ alkenyl; aryl$(C_2-C_6)$alkenyl and linear or branched $(C_2-C_6)$ alkynyl, which process comprises:

(a) reacting a compound of formula (X):

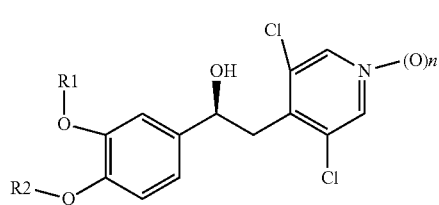

(X)

wherein n is 0 or 1, with a compound of formula (III):

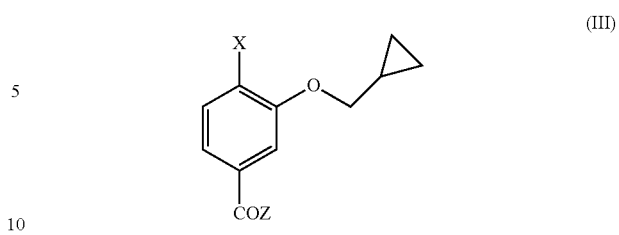

(III)

wherein X is selected from —NHSO$_2$Me and —NO$_2$ and Z is selected from —OH, chlorine, bromine, linear or branched $(C_1-C_6)$alkoxy, aryloxy, arylalkoxy, $(C_1-C_6)$alkylcarbonyloxy, arylcarbonyloxy and aryl$(C_1-C_6)$alkylcarbonyloxy, to obtain a compound of formula (XI) wherein n is 0 or 1 or a compound of formula (XII):

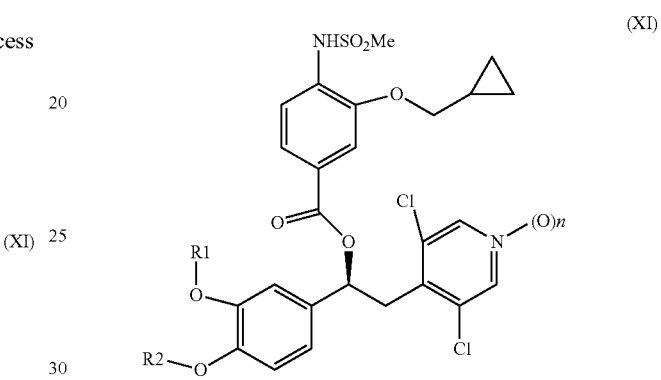

(XI)

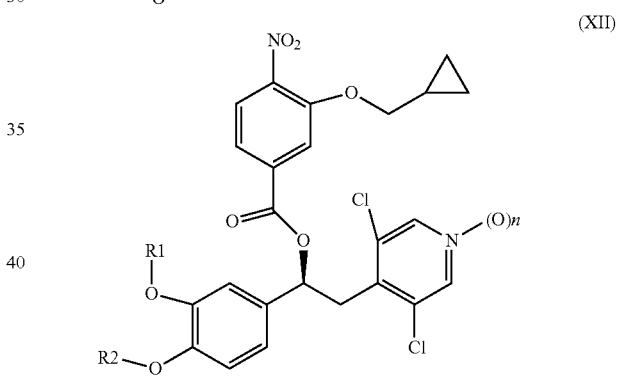

(XII)

wherein R1, R2, and n have the above reported meanings; and, when a compound of formula (XII) is obtained in step (a):

(b) reducing it to a corresponding compound of formula (XIII):

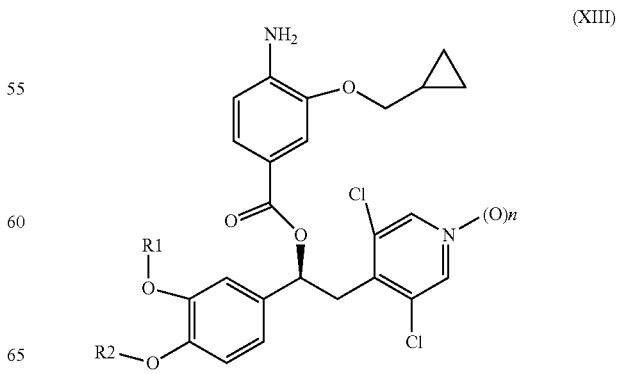

(XIII)

wherein R1, R2, and n have the above reported meanings, and reacting it with methanesulfonyl halide to obtain a compound of formula (XI) wherein n has the above reported meanings;

and wherein the compound of formula (X) in step (a) is obtained according to any one of the alternative steps (c1) or (c2) by:

(c1) oxidizing a compound of formula (XIV):

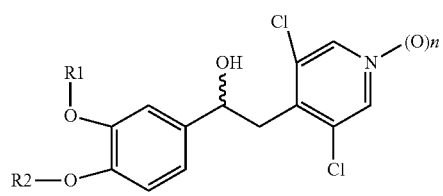

wherein n is 0 or 1 to obtain a compound of formula (XV):

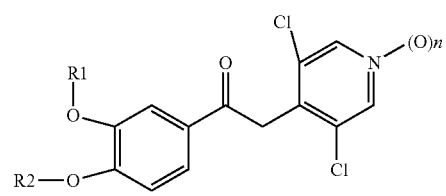

wherein n is 0 or 1, and subsequently enantioselectively reducing it to obtain a compound of formula (X) wherein n has the above reported meanings; or (c2) chromatographically separating a compound of formula (XIV) wherein n is 0 or 1, to obtain both a compound of formula (X) and a compound of formula (XVI):

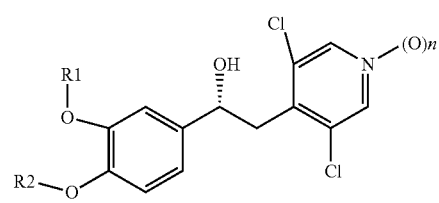

wherein n has the above reported meanings;
and optionally oxidizing the compound of formula (XVI) obtained in step (c2) to a corresponding compound of formula (XV) to be subsequently reduced to a compound of formula (XIV) wherein n is 0 or 1 and reprocessed in the following chromatographic separation process;

and wherein all of the compounds of formula (XI), (X), (XII), (XIII), (XIV), (XV) or (XVI) wherein n is 1 can be obtained by oxidizing the corresponding compounds wherein n is 0.

From all of the above, it is clear that the operative conditions applicable to the aforementioned steps of the process for the preparation of the compounds of formula (I) may apply as well to the preparation of the compounds of formula (XI).

The intermediates compounds of formula (XII) and (XIII) and wherein n is 0 or 1 are novel and, hence, represent a further embodiment of the present invention.

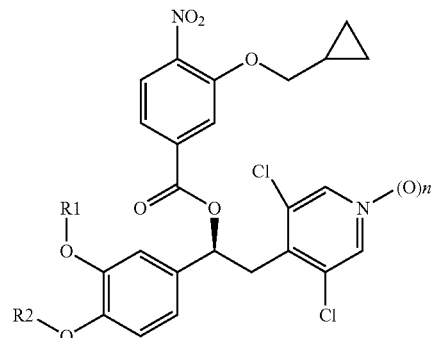

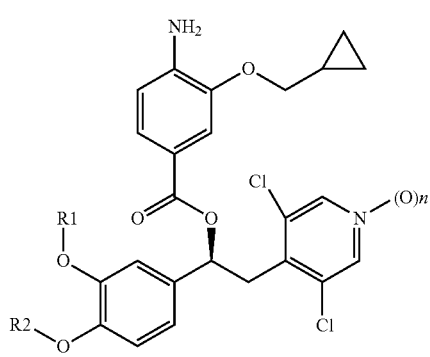

The starting material of formula (X) is known or readily prepared according to known methods.

In a further even more preferred embodiment, when compound (I) wherein n is 0 or 1 is obtained, it may be purified by crystallization or crushing from one or more solvents preferably selected from water, methanol, ethanol, isopropanol, n-butanol, t-butanol, toluene, benzene, xylene, acetone, isopropyl ketone, methyl ethyl ketone, methyl isobutyl ketone, THF, dioxane, 2-methoxyethyl ether, diethyl ether, isopropyl ether, t-butyl methyl ether, ethyl acetate, isopropyl acetate, dichloromethane, an aliphatic or aromatic hydrocarbon, preferably chosen from the group consisting of pentane, hexane, heptane, cyclohexane, and methylcyclohexane or mixture thereof.

The reaction is preferably carried out in ethyl acetate with n-heptane.

In another preferred embodiment, the present invention relates to the process for the isolation by crystallization of the compound (I) and to its use for the preparation of pharmaceutical compositions for inhalation in combination with suitable carriers or vehicles.

In another preferred embodiment, the present invention provides a process for the preparation of Cystal Form A from ethyl acetate and n-heptane, characterized by the following characteristic XRPD peaks: 7.48; 7.93; 8.55; 10.15; 10.32; 12.72; 13.51; 16.18; 16.46; 17.79; 18.08; 18.53; 18.94; 19.1; 19.89; 20.2; 21.37; 22.96; 23.63; 24.87; 25.82; 26.51; 28.09; and 28.61±0.2 degrees/2 theta.

In another preferred embodiment, the present invention is directed to the use of Crystal Form A for the prevention and/or treatment of an inflammatory or obstructive respiratory disease such as asthma or chronic obstructive pulmonary disease (COPD).

In a still further aspect, the present invention is directed to a method of preventing and/or treating an inflammatory or obstructive respiratory disease such as asthma or chronic obstructive pulmonary disease (COPD), which comprises the inhalatory administration of an effective amount of Crystal Form A.

In another preferred embodiment, the present invention is directed to a process for the preparation of solvates of a compound of formula (I).

In another preferred embodiment, the invention is directed to a process for the preparation of a solvate of a compound of formula (I) from ethanol, characterized by the following characteristic XRPD peaks: 7.45; 7.87; 8.51; 10.12; 10.28; 12.66; 13.29; 13.45; 14.95; 16.14; 16.34; 17.05; 17.74; 18.05; 18.48; 18.88; 19.05; 19.33; 19.85; 20.18; 20.65; 21.3; 22.96; 23.55; 23.87; 24.41; 24.66; 24.88; 25.62; 25.82; 26.45; 28.12; and 28.53±0.2 degrees/2 theta.

Pharmaceutical compositions can be prepared by admixture of compounds of formula (I) wherein n is 0 or 1 prepared according to the present invention and one or more pharmaceutically acceptable excipients. Depending on the nature of the medical disease or condition to be treated, and the type of patient, the pharmaceutical compositions may be formulated to be delivered by any suitable route, including oral, intravenous, parenteral, inhalation, intranasal, topical, subcutaneous, intramuscular, rectal, vaginal. Suitable dosage forms include known formulations such as tablets, capsules, powders, sustained release formulations, ointments, gels, creams, suppositories, eye drops, transdermal patches, syrups, solutions, suspensions, aerosols, solutions for nebulizers, nasal sprays etc. In a preferred embodiment the composition is formulated for delivery by the inhalation or intranasal routes, for instance in an aerosol solution or suspension, as a dry powder for inhalation, or in a nasal spray.

Suitable excipients include carriers, diluents, wetting agents, emulsifying agents, binders, coatings, fillers, glidants, lubricants, disintegrants, preservatives, surfactants, pH buffering substances and the like. Examples of excipients and their use are provided in the Handbook of Pharmaceutical Excipients, $5^{th}$ ed. (2006), Ed. Rowe et al., Pharmaceutical Press, which is incorporated herein by reference in its entirety.

The dosages of the compounds of the present invention may depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula (I) wherein n is 0 or 1 may be administered for example, at a dosage comprised between 0.001 and 1000 mg/day, preferably between 0.1 and 500 mg/day, even more preferably between 0.2 and 2000 mg/day and even more preferably between 0.1 and 4000 mg/day.

Compounds of formula (I) wherein n is 0 or 1 obtained according to the invention may be used for prophylactic purposes or for symptomatic relief for a wide range of conditions including: respiratory disorders such as chronic bronchitis, chronic obstructive pulmonary disease (COPD) and asthma of all types. However the compounds of formula (I) wherein n is 0 or 1 may be administered for the prevention and/or treatment of any disease wherein the activity of PDE4 receptors is implicated and inhibition of PDE4 receptor activity is desired, or a disease state which is mediated by PDE4 activity (for instance a disease state in which PDE4 is overexpressed or overactive). Examples of such diseases include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, atherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, itching in the anogenital area, alopecia areata, hypertrophic scars, discoid lupus erythematosus, systemic lupus erythematosus, follicular and wide-area pyodermias, endogenous and exogenous acne, acne rosacea, Behcet's disease, anaphylactoid purpura nephritis, inflammatory bowel disease, leukemia, multiple sclerosis, gastrointestinal diseases, autoimmune diseases, and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

In one embodiment, the present invention provides the use of compounds of formula (I) wherein n is 0 or 1 prepared according to any of the methods of the invention, in the manufacture of a medicament for the prevention or treatment of any of chronic bronchitis, chronic obstructive pulmonary disease (COPD), asthma of all types, atopic dermatitis, and allergic rhinitis.

In a further embodiment, the present invention provides a method for prevention of treatment of any of chronic bronchitis, chronic obstructive pulmonary disease (COPD), asthma of all types, atopic dermatitis and allergic rhinitis in a patient, comprising the administration to the patient of a therapeutically effective amount of compounds of formula (I) wherein n is 0 or 1 prepared according to any of the methods of the invention.

A "therapeutically effective amount" of substance is defined herein as an amount leading to a detectable improvement in one or more clinical symptoms of the treated condition or measurably reducing the probability of development of a disease condition or its symptoms.

The present invention is further explained by reference to the following Schemes 1-6.

Scheme 1
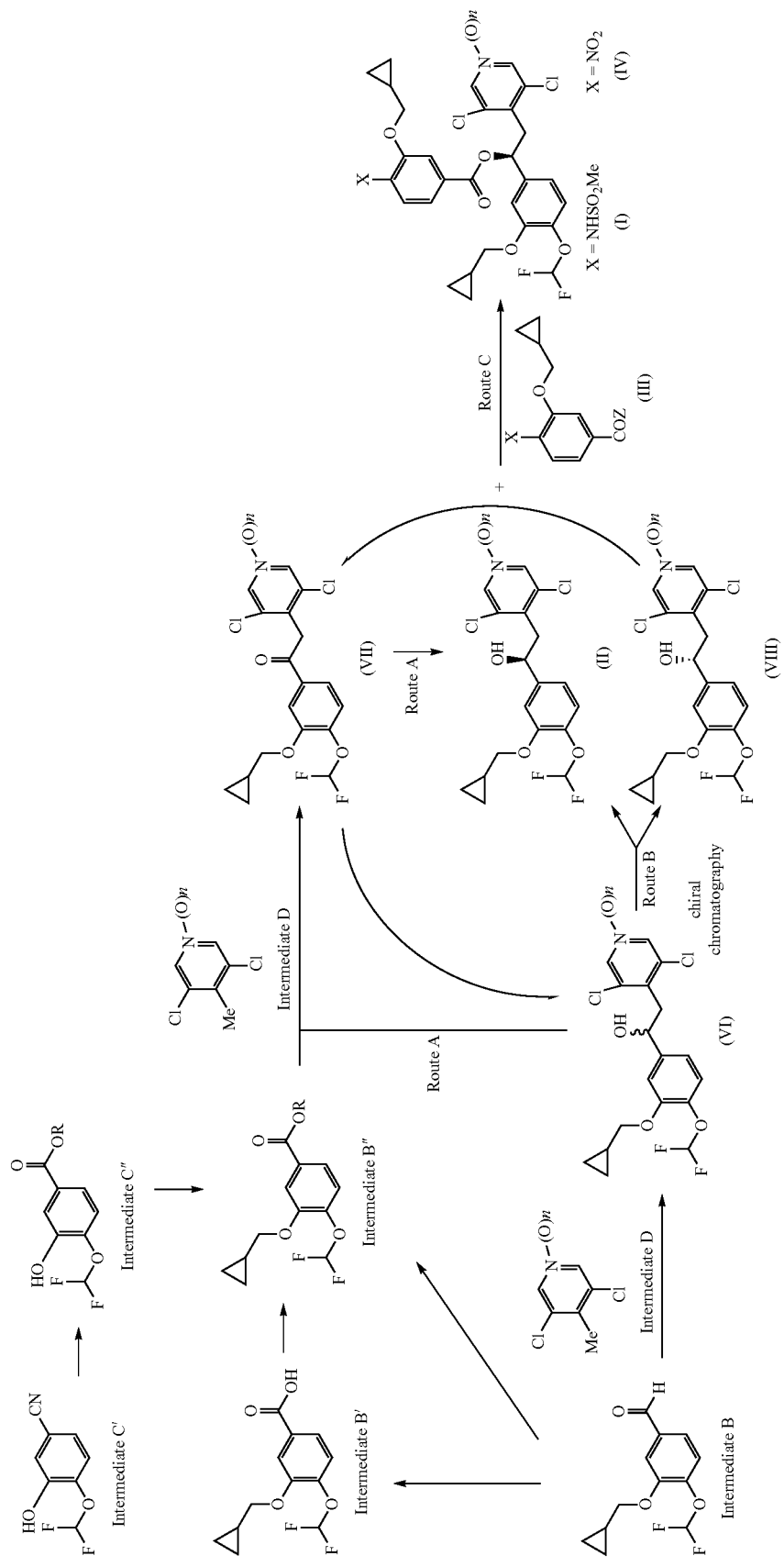

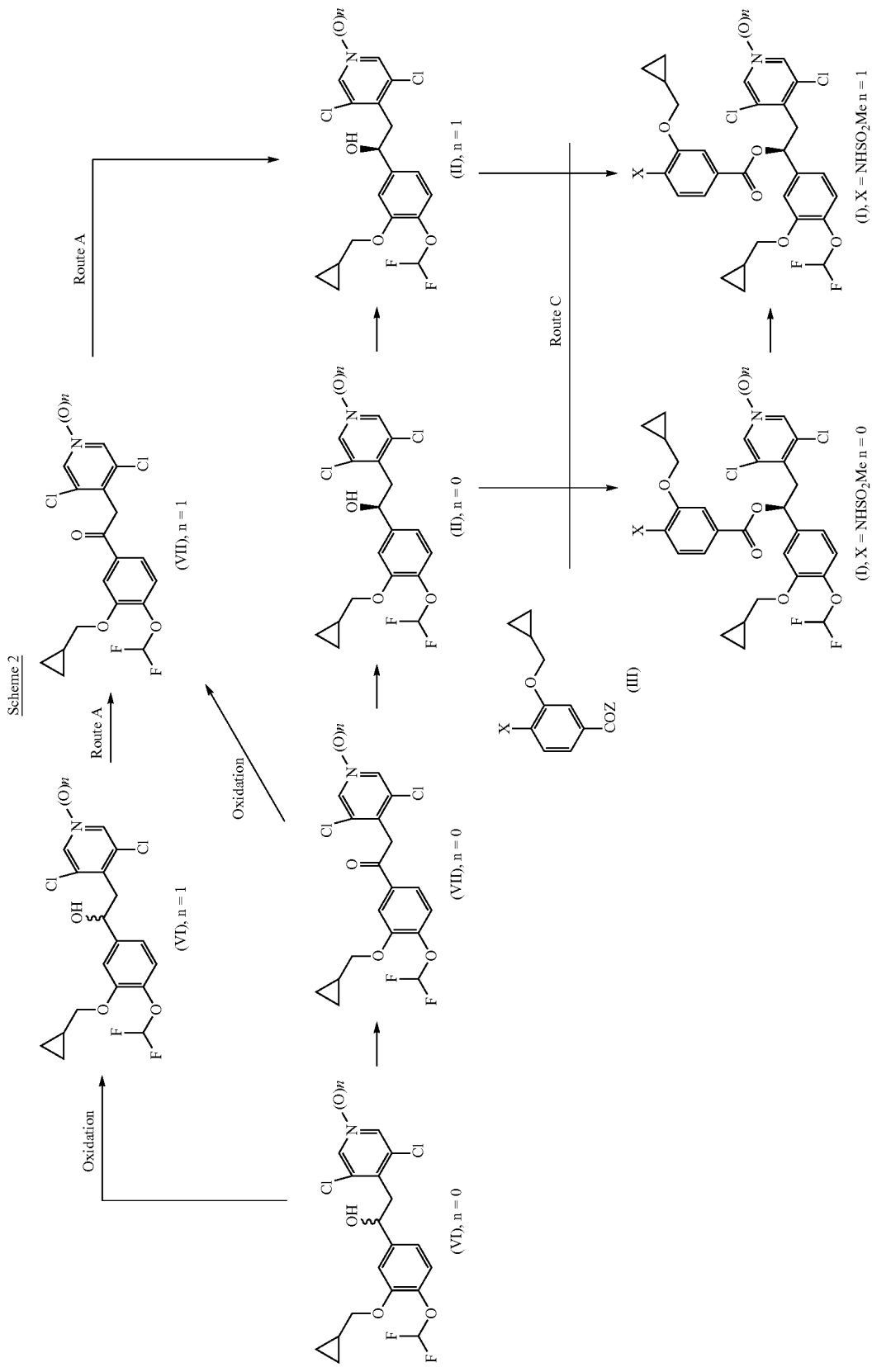

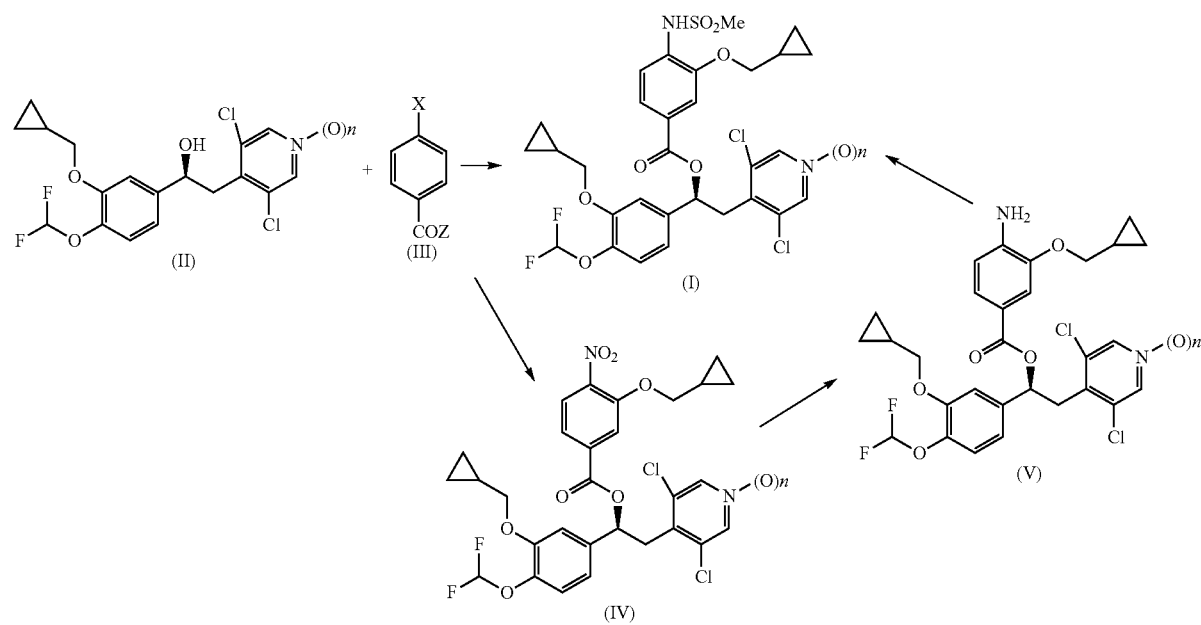

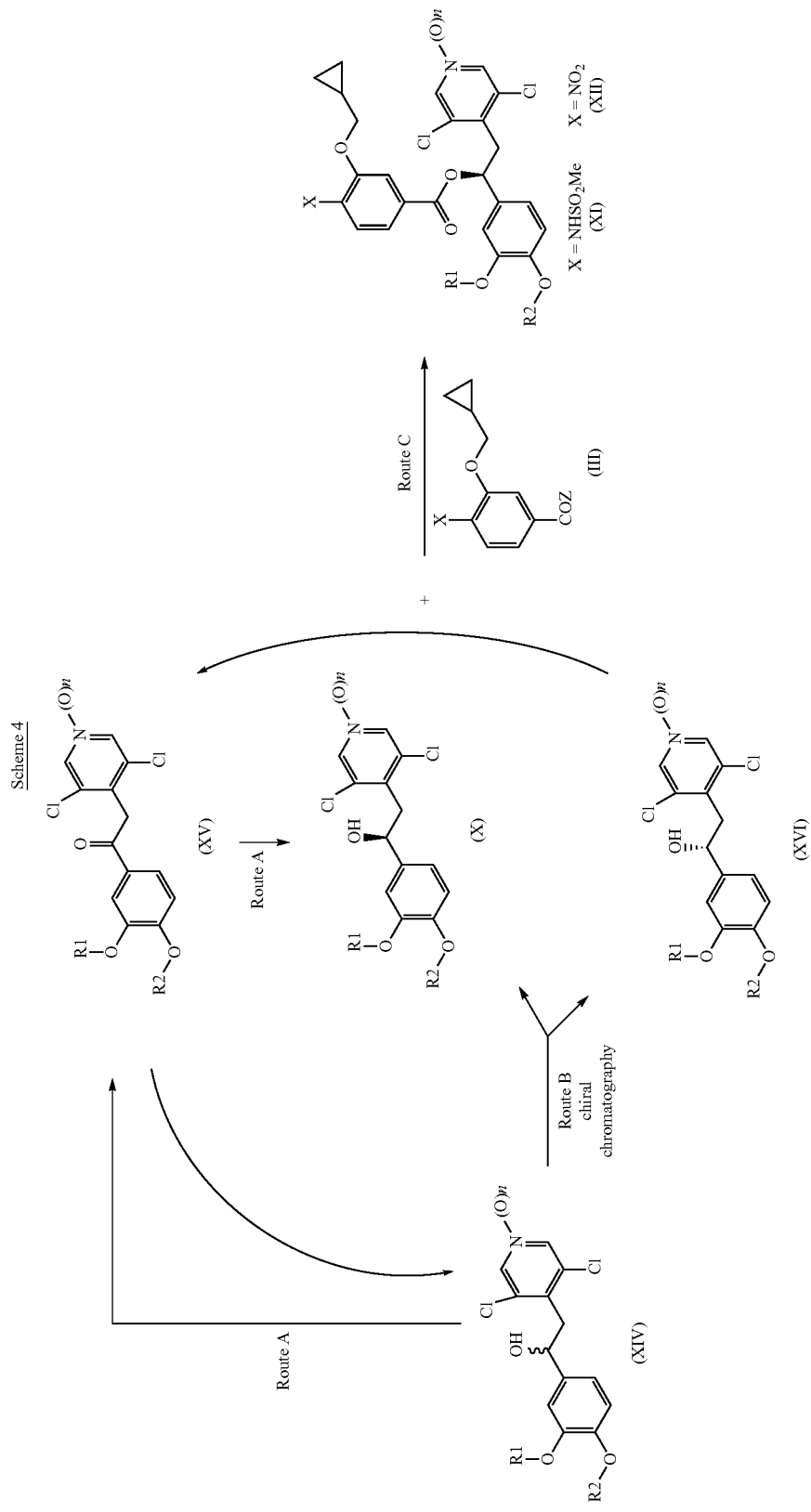

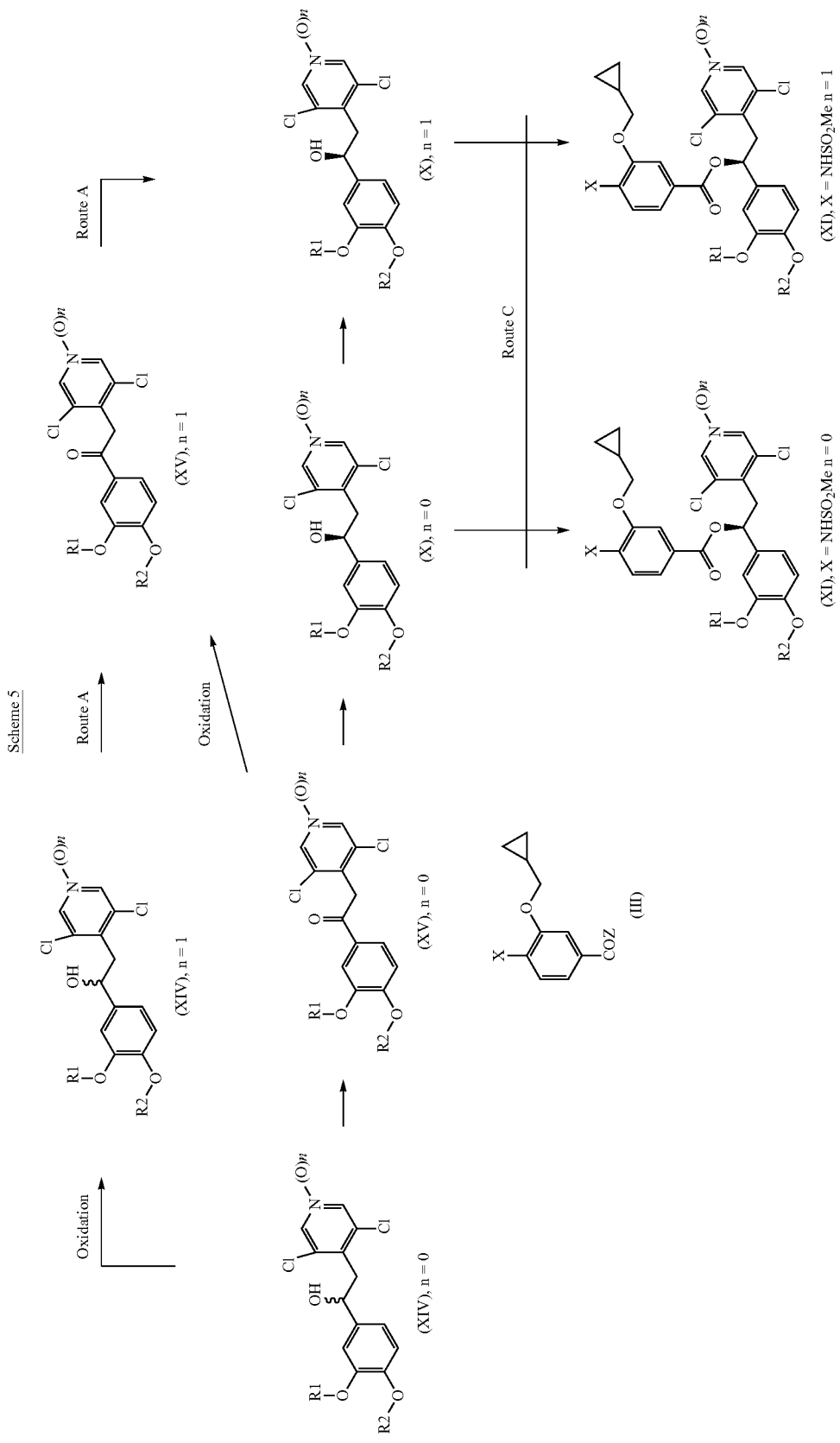

Scheme 6

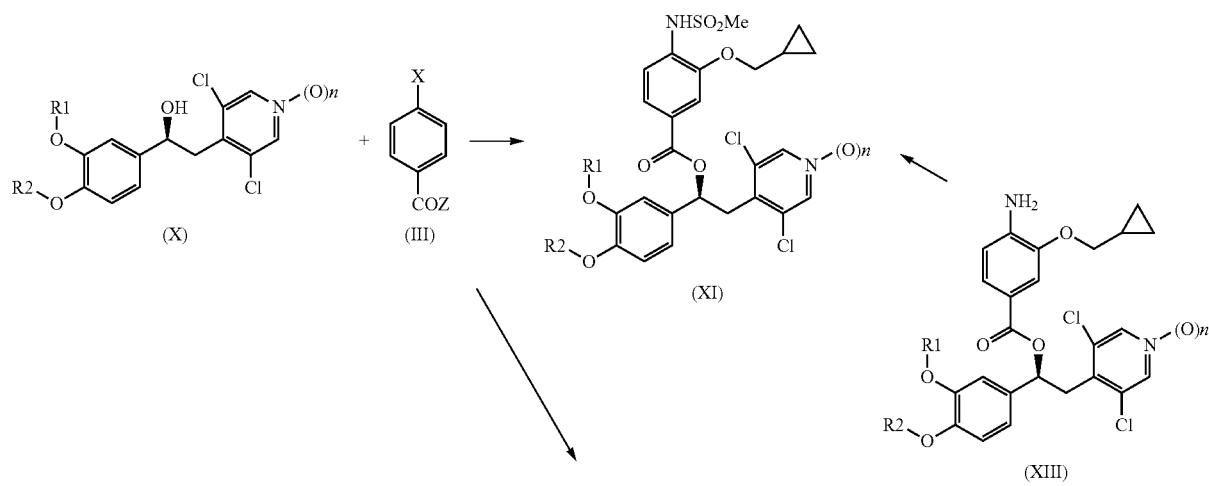

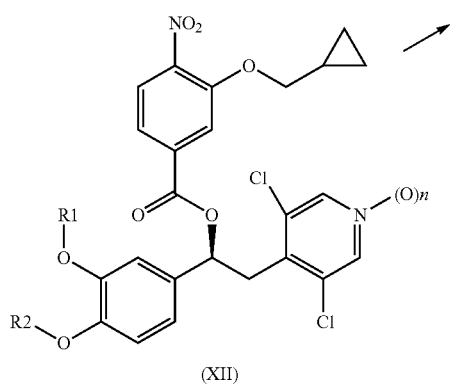

The present invention provides a method for preparing a compound a general formula (I) wherein n is 0 or 1 according to the following steps.

Route A—intermediate (VI) wherein n is 0 or 1, obtained according to the procedure described in WO 2010/089107, which is incorporated herein by reference in its entirety, Example 1, is oxidized to (VII) wherein n is 0 or 1 in presence of an oxidizing agent selected from a metallic oxide such as $MnO_2$, a hypervalent iodine, like 2-Iodoxybenzoic acid (IBX) or Dess-Martin periodinate, dimethylsulfoxide-based oxidants (Swern) like Sulfur trioxide pyridine complex. The synthesis is preferably carried out in a solvent selected from water, dimethyl formamide, dimethyl acetamide, N-methyl pyrrolidone, dimethyl sulfoxide, sulfolane, toluene, benzene, xylene, acetone, isopropyl ketone, methyl ethyl ketone, methyl isobutyl ketone, ethyl acetate, isopropyl acetate, acetonitrile, dichloromethane, tetrahydrofuran (THF), dioxane and mixtures thereof. The reaction is preferably carried out with $MnO_2$ in toluene or with a Swern oxidant in DMSO.

Alternatively compound of formula (VII) can be obtained reacting an intermediate of formula B":

Intermediate B"

wherein R is a linear or branched ($C_1$-$C_6$) alkyl group or a arylalkyl group, with an intermediate of formula D:

Intermediate D

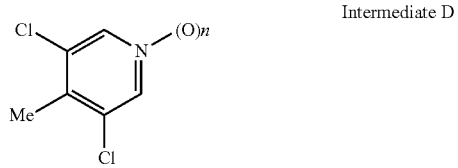

wherein n has the above reported meanings, in presence of a base preferably selected from lithium diisopropylamide (LDA), butyl lithium, hexyl lithium, pentyl lithium, lithium bis(trimethylsilyl)amide (LHMDS), sodium bis(trimethylsilyl)-amide, and potassium t-butylate, in the presence of suitable solvents such as toluene, benzene, xylene, tetrahydrofuran, methyl-tetrahydrofuran, dioxane, 2-methoxyethyl ether, diethyl ether, isopropyl ether, t-butylmethyl ether, and mixtures thereof.

More preferably, R is methyl and the above reaction is conducted with LHMDS in THF.

Compound B" can be obtained from compound B' by reaction with thionyl chloride, hydrochloric acid, sulfuric acid in methanol, ethanol, isopropanol, n-butanol, t-butanol, benzyl alcohol with or without other solvents, or by reaction with the relative alkyl halide in the presence of suitable solvents such as methanol, ethanol, isopropanol, n-butanol, t-butanol, dimethyl formamide, dimethyl acetamide, N-methyl pyrrolidone, tetrahydrofuran, dioxane, ethyl acetate, isopropyl acetate, acetonitrile, dichloromethane, and mixtures thereof and a base preferably selected from sodium hydroxide, sodium carbonate, sodium bicarbonate, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethylamine), NMM (N-Methylmorpholine), and pyridine.

More preferably, the above reaction is conducted with potassium carbonate in dimethyl formamide or dimethyl acetamide.

Compound B' can be obtained from compound B with an oxidizing agent selected from hydrogen peroxide, an organic peracid, like paracetic acid, or m-chloroperbenzoic acid, or a mineral peracid like persolforic acid, or Oxone® ($KHSO_5*½KHSO_4*½K_2SO_4$), in the presence of suitable solvents such as water, methanol, ethanol, isopropanol, n-butanol, t-butanol, dimethyl formamide, dimethyl acetamide, N-methyl pyrrolidone, tetrahydrofuran, dioxane, 2-methoxyethyl ether, isopropyl acetate, acetonitrile, and mixtures thereof. More preferably, the above reaction is conducted with Oxone® in methanol.

Alternatively intermediate of formula B" can be obtained from intermediate of formula C" by alkylation with Bromomethylcyclopropane in presence of a base preferably selected from sodium hydroxide, sodium carbonate, sodium bicarbonate, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethyl-amine), NMM (N-Methylmorpholine), pyridine, DBU, DBO, and DMAP and in a suitable solvent such as methanol, ethanol, isopropanol, n-butanol, t-butanol, dimethyl formamide, dimethyl acetamide, N-methyl pyrrolidone, tetrahydrofuran, dioxane, 2-methoxyethyl ether, diethyl ether, isopropyl ether, t-butyl methyl ether, ethyl acetate, isopropyl acetate, acetonitrile, dichloromethane, and mixtures thereof. More preferably, the above reaction is conducted with potassium carbonate in dimethyl formamide.

Intermediate C" can be obtained from intermediate C' by Pinner reaction in presence of an alcohol and a Lewis acid selected from hydrogen chloride, hydrogen bromide, sulfuric acid, alkane sulphonic acids like methane sulfonic acid, aryl sulphonic acids like benzene sulfonic acid, aluminium tribromide, aluminium trichloride, titanium(IV) tetrachloride, Titanium(IV) isopropoxide Tin(IV) chloride, boron trifluoride, Boron trichloride, Iron(III) chloride, Iron(III) bromide, Aluminum isopropoxide, thionyl chloride, oxalyl chloride, trimethylsilyl chloride (TMSCl), and trimethylsilyl triflate (Me3SiOTf), with or without a suitable solvent such as dimethyl formamide, dimethyl acetamide, N-methyl pyrrolidone, toluene, benzene, xylene, tetrahydrofuran, dioxane, 2-methoxyethyl ether, diethyl ether, isopropyl ether, t-butyl methyl ether, and mixtures thereof. More preferably, the above reaction is conducted with sulphuric acid in methanol.

Subsequent enantioselective reduction of (VII) wherein n is 0 or 1 provides the single enantiomer (II) wherein n is 0 or 1.

The reducing agent is selected from hydrogen in presence of a heavy metal chiral complex pre-formed or formed in situ reacting a Ru-, Rh- or Ir-complex such as $RuCl_2(PPh_3)_3$, [Ru (p-cymene) $Cl_2]_2$, [$RhCl_2(Cp*)]_2$ or [$IrCl_2(Cp*)]_2$ with a chiral ligand such as SL-N004-1 ((S)-4-tert-Butyl-2-[(S)-2-(bis(1-phenyl)phosphino)ferrocen-1-yl]oxazoline,), SL-N003-1 ((R)-4-Isopropyl-2-[(R)-2-(diphenylphosphino)-ferrocen-1-yl]Oxazoline), (S,S)-Ts-DPEN ((1S,2S)-(–)-N-p-tosyl-1,2-diphenylethylenediamine), (S,S)-Ms-DPEN ((1S,2S)-(–)-N-Mesyl-1,2-diphenylethylenediamine), (R)-DAIPEN ((2R)-(–)-1,1-Bis(4-methoxyphenyl)-3-methyl-1,2-butanediamine), or (1R,2S)-1-Amino-2-indanol. The reaction is conducted in presence of a base, preferably selected from sodium hydroxide, sodium carbonate, sodium $C_1$-$C_4$ alcoholates, sodium bicarbonate, sodium hydride, potassium hydroxide, potassium carbonate, potassium $C_1$-$C_4$ alcoholates, potassium bicarbonate, lithium hydroxide, lithium carbonate, lithium $C_1$-$C_4$ alcoholates, caesium hydroxide, caesium carbonate, caesium bicarbonate, triethyl amine, pyridine, and 4-dimethylaminopyridine.

The synthesis is preferably carried out in a solvent selected from water, methanol, ethanol, isopropanol, n-butanol, t-butanol, dimethyl formamide, dimethyl acetamide, N-methyl pyrrolidone, toluene, benzene, xylene, THF, dioxane, 2-methoxyethyl ether, diethyl ether, isopropyl ether, t-butyl methyl ether, ethyl acetate, isopropyl acetate, acetonitrile, and mixtures thereof.

The reaction is preferably carried out with the complex formed in situ by reacting $RuCl_2(PPh_3)_3$ and the chiral ligand SL-N004-1 in toluene in presence of aqueous sodium hydroxide.

Alternatively, (II) wherein n is 1 is obtained by oxidation of (II) wherein n is 0 with an oxidizing agent selected from hydrogen peroxide, an organic peracid, like paracetic acid, or m-chloroperbenzoic acid, or a mineral peracid like persolforic acid or Oxone® ($KHSO_5*½KHSO_4*½K_2SO_4$). Reaction solvent is selected from water, methanol, ethanol, isopropanol, n-butanol, t-butanol, dimethyl formamide, dimethyl acetamide, N-methyl pyrrolidone, toluene, benzene, xylene, acetone, isopropyl ketone, methyl ethyl ketone, methyl isobutyl ketone, THF, dioxane, ethyl acetate, isopropyl acetate, acetonitrile, acetic acid, and mixtures thereof. The reaction is preferably conducted with Oxone® in water and methanol.

Route B—In alternative to Route A, intermediates (II) and (VIII) wherein n is 0 or 1 are obtained from (VI) wherein n is 0 or 1 by preparative chiral HPLC separation of the enantiomers.

A batch procedure may be adopted loading the chiral column with a solution of racemic (VI) in several runs and collecting the eluted fractions of separated enantiomers. A simulated moving bed (SMB) procedure should be considered to separate large amount of material.

Once the compounds of formula (II) and (VIII) have been separated through preparative chiral HPLC techniques, the compound of formula (VIII) may be conveniently reconverted into the compound of formula (VI) through oxidation to the corresponding derivative of formula (VII) and subsequent reduction and reprocessed in the chromatographic separation process, as formerly described.

In this way, by recycling (VIII), final yields of compound of formula (I) can be further increased.

In intermediate (III), wherein X is —NHSO$_2$Me and Z is selected from —OH, chlorine, bromine, linear or branched ($C_1$-$C_6$)alkoxy, aryloxy, arylalkoxy, ($C_1$-$C_6$)alkylcarbonyloxy, arylcarbonyloxy and aryl($C_1$-$C_6$)alkylcarbonyloxy, Z is a protecting group that can be introduced and removed using standard procedures according to "Protective Groups in Organic Synthesis" by Theodora W. Greene (Wiley-Interscience, New York, 1981) and "Protective Groups in Organic Chemistry" by J. F. W. McOmie (Plenum Press, London, 1973), which is incorporated herein by reference in its entirety.

Intermediate (III), wherein X is —NHSO$_2$Me and Z is as defined above, can be therefore obtained under well-known conditions starting from 3-cyclopropylmethoxy-4-metanesulfonylamino-benzoic acid methyl ester, obtained as described in WO2007/089107, which is incorporated herein by reference in its entirety, Example 18 or according to the same synthesis route starting from the relative ester of the 3-hydroxy-4-nitrobenzoic acid.

Intermediate (III), wherein X is —NHSO$_2$Me and Z is as defined above, converts to (III) wherein Z is —OH by hydrolysis in a base, preferably selected from the group consisting of sodium hydroxide, sodium carbonate, potassium hydroxide, potassium carbonate, lithium hydroxide, lithium carbonate, caesium hydroxide, and caesium carbonate; the solvent is selected from water alone or in mixture with methanol, ethanol, isopropanol, n-butanol, t-butanol, dimethyl sulfoxide, sulfolane, toluene, benzene, xylene, THF, dioxane, and mixtures thereof In a preferred embodiment the reaction is carried out with NaOH in THF and water.

Route C—compound (I) wherein n is 0 or 1 is obtained by condensing intermediate (III) wherein X is —NHSO$_2$Me and Z is —OH, with (II) wherein n is 0 or 1 in presence of a coupling reagent selected from CDI (1,1'-Carbonyldiimidazole), HATU (1-[Bis(dimethylamino)methylene]-1H-1,2,3-triazolo[4,5-b]pyridinium 3-oxid hexafluorophosphate), HBTU (O-(Benzotriazol-1-yl)-N,N,N',N'-tetramethyluronium hexafluorophosphate), TBTU (O-(Benzotriazol-1-yl)-N,N,N',N'-tetramethyluronium tetrafluoroborate), DMTMM (4-(4,6-Dimethoxy-1,3,5-triazin-2-yl)-4-methylmorpholinium chloride), COMU ((1-Cyano-2-ethoxy-2-oxoethylidenaminooxy)dimethylamino-morpholino-carbenium hexafluorophosphate), EDCI (N-(3-Dimethylaminopropyl)-N'-ethylcarbodiimide hydrochloride), and DCC (N,N'-Dicyclohexylcarbodiimide), or a reagent that can convert the carboxylic acid into a acyl chloride, an acyl bromide, an activate ester or a mixed anhydride, with or without HOBt (1-Hydroxybenzotriazole), with or without an organic base like TEA, DIPEA, NMM, DBU, DBO, pyridine, and DMAP in a solvent selected from the group consisting of dimethyl sulfoxide, sulfolane, dimethyl formamide, dimethyl acetamide, N-methyl pyrrolidone, toluene, benzene, xylene, acetone, isopropyl ketone, methyl ethyl ketone, methyl isobutyl ketone, THF, dioxane, 2-methoxyethyl ether, diethyl ether, isopropyl ether, t-butyl methyl ether, ethyl acetate, isopropyl acetate, acetonitrile, dichloromethane, chloroform, chlorobenzene, and mixtures thereof.

When the compound of formula (III) is an acyl chloride or bromide, or an activated ester and a mixed anhydride, the reaction is carried out as above described without the presence of a coupling reagent.

In a preferred embodiment the reaction is conducted with CDI and DBU in ethyl acetate.

Intermediate (IV), wherein n is 0 or 1, is obtained by condensation of (III) wherein X is —NO$_2$, with (II) wherein n is 0 or 1, under the same conditions described above for the condensation of (III) wherein X is —NHSO$_2$Me with (II). In a preferred embodiment the reaction is conducted with EDCI and DMAP in DMF.

Intermediate (V), wherein n is 0 or 1, is obtained by reducing (IV), wherein n is 0 or 1, with a reducing agent selected from the group consisting of hydrogen, cyclohexadiene, ammonium formate, formic acid, iron, tin dichloride, tin, nickel chloride, nickel, lithium aluminium hydride, sodium aluminium hydride, lithium borohydride, sodium borohydride, and potassium borohydride sodium hydrosulfite. In the case of the employment of hydrogen, cyclohexadiene, ammonium formate, and formic acid the reaction is carried out in the presence of a catalyst, preferably palladium- platinum- or nickel-based, more preferably selected from palladium on carbon, palladium on barium sulphate, and palladium on calcium carbonate. When formic acid is used, the reaction is carried out in the presence of ammonia or an amine, preferably triethylamine.

Suitable solvents for the above reducing steps are selected from water, methanol, ethanol, isopropanol, n-butanol, t-butanol, dimethyl formamide, dimethyl acetamide, N-methyl pyrrolidone, toluene, benzene, xylene, THF, dioxane, 2-methoxyethyl ether, diethyl ether, isopropyl ether, t-butyl methyl ether, ethyl acetate, isopropyl acetate, acetonitrile, and mixtures thereof. In a preferred embodiment the reaction is carried out with hydrogen with palladium 5% on activated carbon powder, type A103038, sulfided in ethyl acetate.

In another preferred embodiment, the reaction is carried out with hydrogen with platinum on charcoal in ethyl acetate.

Compound (I), wherein n is 0 or 1, is obtained by reacting (V), wherein n is 0 or 1, with methanesulfonyl chloride in the presence of suitable solvents selected from toluene, benzene, xylene, tetrahydrofuran, dioxane, 2-methoxyethyl ether, diethyl ether, isopropyl ether, t-buthylmethyl ether, ethyl acetate, isopropyl acetate, acetonitrile, dichloromethane, chloroform, chlorobenzene, and mixtures thereof and a base preferably selected from the group consisting of sodium hydroxide, sodium carbonate, sodium bicarbonate, sodium hydride, potassium hydroxide, potassium carbonate, potassium bicarbonate, lithium hydroxide, lithium carbonate, caesium hydroxide, caesium carbonate, caesium bicarbonate, TEA (triethylamine), DIPEA (Hünig Base, diisopropylethyl-amine), NMM (N-Methylmorpholine) DBU (1,8-Diazabicyclo[5.4.0]undec-7-ene), DBO (1,4-Diazabicyclo[2.2.2]octane), pyridine, and DMAP (4-dimethylaminopyridine), pyridine; in the case when pyridine is used in excess other solvents can be avoided.

The reaction is preferably carried out with triethylamine in dichloromethane.

All the compounds of formula (I), (II), (IV), (V), (VI), (VII) or (VIII) wherein n is 1 can be obtained by oxidizing the corresponding compounds wherein n is 0, as described above for the oxidation of compound (II) wherein n is 0 to compound (II) wherein n is 1.

When compound (I) wherein n is 0 or 1 is obtained, it may be purified by crystallization or crushing from one or more solvents preferably selected from water, methanol, ethanol, isopropanol, n-butanol, t-butanol, toluene, benzene, xylene, acetone, isopropyl ketone, methyl ethyl ketone, methyl isobutyl ketone, THF, dioxane, 2-methoxyethyl ether, diethyl ether, isopropyl ether, t-butyl methyl ether, ethyl acetate, isopropyl acetate, dichloromethane, an aliphatic or aromatic hydrocarbon, preferably chosen from the group consisting in pentane, hexane, heptane, cyclohexane and methylcyclohexane or mixture thereof. The reaction is preferably carried out in ethyl acetate with n-heptane.

Thus, for example, Crystalline Form A may be prepared in presence of ethyl acetate/heptane, or isopropyl acetate.

The reaction may be carried out in a reactor, wherein compound of formula (I) is loaded together with one or more solvents selected from the above list, and the suspension may be stirred while heating to a temperature between 50 to 90° C. until complete dissolution of the solid. The suspension may be cooled down between 0 to 5° C. for 1 to 5 hours, filtered and dried.

When the crystallization is carried out in presence of ethanol, a solvate of compound of formula (I) may be obtained.

The reaction may be carried out starting from a compound of formula (I), in one or more solvents selected from the group consisting of pentane, hexane, heptane, cyclohexane, methylcyclohexane and dichloromethane, obtaining a solution that may be concentrated and then added with ethanol. The solution may be concentrated and the obtained suspension may be cooled at a temperature between 0 to 10° C. and stirred for 1 to 5 hours. The solid filtered, washed with ethanol and dried at a temperature between 25 to 55° C. for 10 to 30 hours.

Other features of the invention will become apparent in the course of the following descriptions of exemplary embodiments which are given for illustration of the invention and are not intended to be limiting thereof.

EXAMPLES

Example 1

Preparation of 3-(cyclopropylmethoxy)-4-(methylsulfonamido)benzoic acid (intermediate (III), X=—NHSO$_2$Me, Z=—OH)

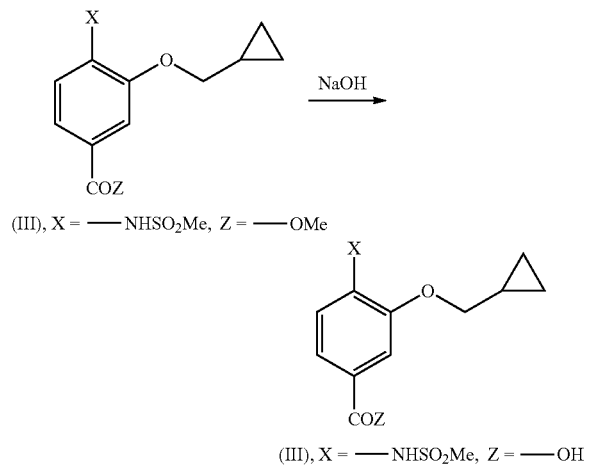

(III) Wherein X is —NHSO$_2$Me and Z is —OMe was obtained as described in WO 2010/08910, which is incorporated herein by reference in its entirety, Example 18. It (6.0 kg) and 18 L of THF were loaded into a reactor. Separately, 6.6 kg of 35% w/w sodium hydroxide and 21 L of purified water were mixed and transferred into the reactor, and the mixture was heated up to 65° C. while distilling off all the THF. After the completion of the hydrolytic reaction the basic solution was slowly transferred into another reactor containing a solution of 24 L of purified water and 7.2 kg of 37% w/w hydrochloric acid, keeping the temperature below 40° C. and stirring for 15 minutes. The obtained solid was filtered and washed with 24 L of water. The wet solid (III) (16.6 kg wet) was reloaded in the reactor together with 60 L of ethyl acetate, then heated up to reflux to distill off 30 L of solvent. 12.6 L of heptane were loaded in the reactor and the mixture was kept under stirring for 15-30 minutes. It was then cooled down to 5° C. and kept under stirring for 2 hours. The obtained solid was filtered and the reactor and the cake washed with 12 L of heptane. Wet solid was dried under vacuum in a static tray drier. 6235 g of white solid were obtained (93.9% yield).

$^1$H NMR (400 MHz, DMSO-d$_6$) δ ppm 12.85 (br. s., 1 H), 9.03 (s, 1 H), 7.40-7.71 (m, 2 H), 7.35 (d, J=8.16 Hz, 1 H), 3.91 (d, J=6.84 Hz, 2 H), 3.07 (s, 3 H), 1.11-1.42 (m, 1 H), 0.50-0.67 (m, 2 H), 0.18-0.41 (m, 2 H).

Example 2

Preparation of 1-(3-(cyclopropylmethoxy)-4-(difluoromethoxy)phenyl)-2-(3,5-dichloro-1-pyridin-4-yl)ethanone (intermediate (VII), n=0)

Intermediate (VI) wherein n is 0 was obtained according to the manufacturing procedure described in WO 2010/089107, which is incorporated herein by reference in its entirety, Example 1.

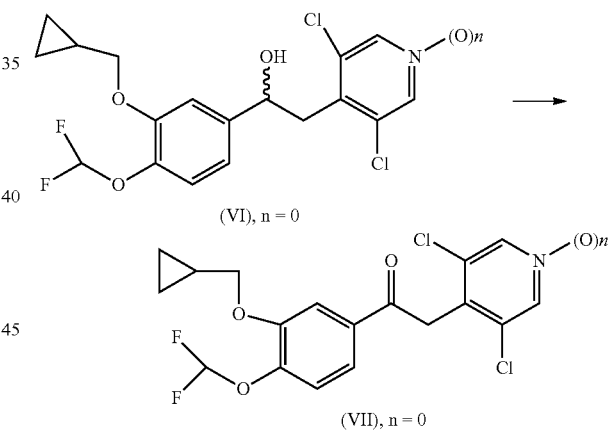

Alternative procedures to obtain intermediate (VII), n=0:
Procedure with MnO$_2$ 5 kg of (VI) wherein n is 0, were dissolved in 30 L of toluene in a reactor; 3.15 kg of activated MnO$_2$ were added into the organic mixture, and the suspension was heated up to reflux for 3 hours. The mixture was cooled down to 50° C. and MnO$_2$ was filtered off on celite pad. The organic solution was loaded in a reactor and toluene was distilled off till to 3 residual volumes. 20 L of 2-propanol was added into reactor and concentrated again till to 2 residual volumes, in order to remove the entire quantity of toluene. Further 20 L of 2-propanol were loaded and the solvent was partially distilled to have 4 residual volumes in the reactor. The suspension was cooled down and kept under stirring at 10° C. overnight. The solid was filtered and the wet solid dried in a vacuum oven at T=50° C. for 12 hours obtaining a white solid (4.12 kg, 82.8% yield).

Product characterization is described in WO 2009018909, which is incorporated herein by reference in its entirety, Example 2 (intermediate 1b).

Procedure Swern

Triethylamine (4.5 mL, 32 mmol) was added dropwise to a solution of alcohol (VI) wherein n is 0, (5.0 g, 12.4 mmol) in DMSO (15 mL), stirring at 25° C. Pyridine. $SO_3$ complex (5.0 g, 3 lmmol) is added portionwise in about 1 hr, so that the internal batch temperature does not rise above 35° C. The reaction mixture is stirred at 25° C. for 4 hours and then quenched with water (60 mL) and 10% aq. $H_2SO_4$ 10% (10 mL). The resulting mixture is stirred at 25° C. and the solid filtered off and desiccated at 50° C. under reduced pressure, to afford 4.6 g (92% yield) of pure ketone (VII) as a colorless solid.

Procedure with IBX (VI) Wherein n is 0, (1.0 g, 2.5 mmol) was added in a single portion to a suspension of 2-Iodoxybenzoic acid (IBX) (0.9 g, 3.2 mmol), prepared according to literature (JOC 1999 pg 4537, which is incorporated herein by reference in its entirety), in DMSO (5 mL), and the resulting mixture was stirred at 25° C. for 1 hour and then to 50° C. for 2 hours. The reaction was quenched with a 10% aq. solution of potassium carbonate (40 mL) after cooling to 25° C. and the solid filtered off to afford ketone (VII) in quantitative yield.

Procedure with sIBX®

Commercially available sIBX® ("Stabilized IBX", a white-powder formulation of IBX composed of a mixture of benzoic acid (22%), isophthalic acid (29%), and o-iodoxybenzoic acid (49%) from SIMAFEX) (2.0 g, 3.2 mmol) was added in a single portion to a solution of (VI) wherein n is 0 (1.0 g, 2.5 mmol) in acetone (15 mL) at 25° C., the resulting mixture was refluxed for 2.5 hours, cooled at 25° C. and then quenched with a 10% aq. solution of sodium sulfite (10 mL) and a 10% aq. solution of potassium carbonate (40 mL). The mixture was stirred at 25° C. for 0.5 hours and the solid filtered off, to afford ketone (VII) wherein n is 0 in quantitative yield.

Procedure with DMP

Dess-Martin periodinane (DMP) (1.3 g, 0.31 mmol) was added in a single portion to a solution of alcohol (VI) wherein n is 0 (1.0 g, 2.5 mmol) in acetone (5 mL). The reaction mixture was stirred at 25-30° C. for 1 hour and quenched with a 10% aq. solution of sodium metabisulfite (10 mL) and 15% aq. sol. of potassium carbonate (30 mL). The mixture was stirred at 25° C. for 0.5 hours and the solid filtered off to afford (VII) wherein n is 0 in quantitative yield.

Example 2A

Preparation of 3,5-dichloro-4-methyl-1-oxy-Pyridine (Intermediate A)

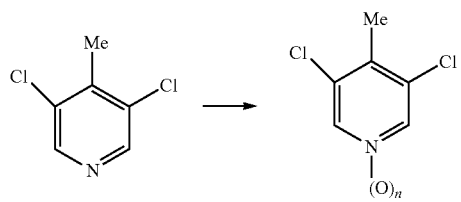

Intermediate A, n = 1

3,5-Dichloro-4-methyl-Pyridine (0.5 g, 3.08 mmol) and Oxone® (1.5 g, 4.62 mmol) were suspended in a 8:3 mixture of methanol and water (5.5 ml) in a 25 ml flask. The suspension was stirred and warmed to 55° C. for 10-15 hours. The solvent was removed under reduce pressure and the obtained crude solid was suspended under stirring in hot Toluene (80° C.) for 20 minutes. The heterogeneous hot solution was then filtrated and the mother liquors were cooled to room temperature obtaining the precipitation of a solid. The pure product was obtained as a white solid after stirring at 0-5° C. for 30 minutes and filtration (0.43 g, 78% yield).

Example 2B

Preparation of (R/S)-1-(3-(cyclopropylmethoxy)-4-(difluoromethoxy)phenyl)-2-(3,5-dichloro-1-oxy-pyridin-4-yl)ethanol (intermediate (VI), n=1)

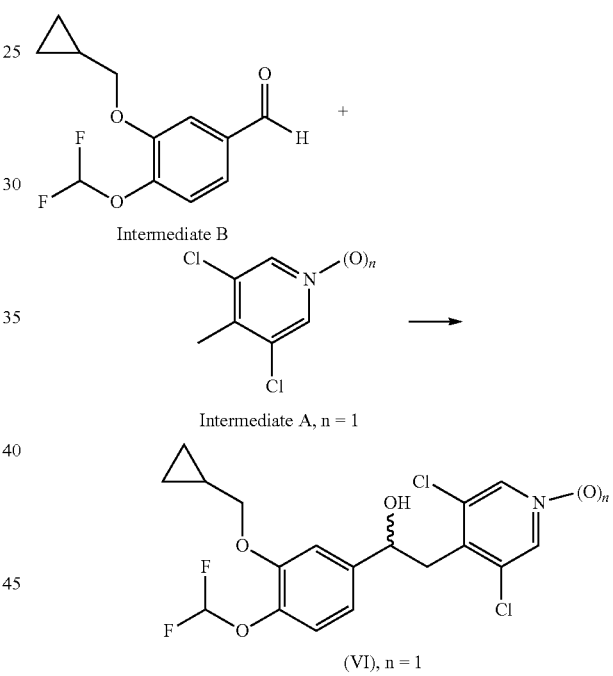

In a three necked 50 ml flask under nitrogen atmosphere Intermediate A (0.4 g, 2.25 mmol) and Intermediate B (0.78 g, 3.22 mmol) were added, and dissolved in dry THF (5 ml). The stirred solution was cooled to −35° C. Potassium tert-butylate (0.3 g, 2.67 mmol) was added portionwise to the solution in 10 minutes. After 60 minutes of reaction at −35° C., the solution is quenched with a 25% aqueous solution of NH4Cl (10 ml). EtOAc (8 ml) and water (8 ml) were added to the suspension and stirred, phases were separated and the organic phase was extracted and washed with a 5% aqueous solution of NaCl (10 ml). The organic solvent was then anydrified on Na2SO4 and removed under reduced pressure obtaining a crude white solid. This was crystallized from hot Toluene obtaining a white solid (0.40 g, 42% yield).

Example 3

Preparation of (R)-1-(3-(cyclopropylmethoxy)-4-(difluoromethoxy)phenyl)-2-(3,5-dichloropyridin-4-yl)ethanol (intermediate (II), n=0)

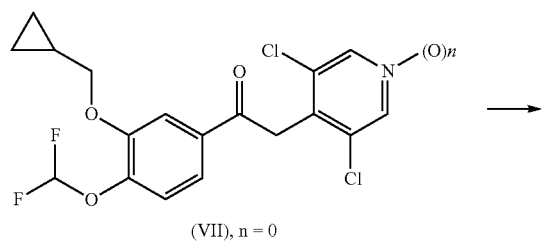

(VII), n = 0

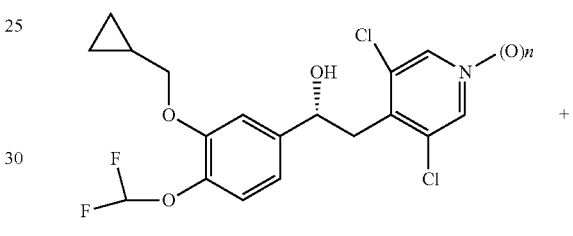

(II), n = 0

2.40 kg of (VII) wherein n is 0 were dissolved in 23L of toluene in a reactor. The reactor was degassed with nitrogen. Solvias proprietary ligand SL-N004-1 and RuCl2(PPh3)3 were placed in a 2 L Schlenk bulb and dried and degassed toluene (1,2 L) was charged. The mixture was heated to 80° C. for 1 hour and then allowed to reach room temperature (RT). The catalyst solution and 298 mL of a degassed aqueous 0.5 M NaOH solution were subsequently added to the reactor. The reactor was closed and degassed with nitrogen and set under 10 bar hydrogen. The mixture was heated to 35° C. under a constant pressure of 10 bars. After a total reaction time of 19 hours, the heater was switched off. The reactor was cooled down to RT and the aqueous layer was removed.

The organic phase was washed twice with 0.5 L of water; aqueous phase was back extracted with 1 L of toluene that was added to the organic phase. 240 g of decolorizing carbon (Norit CAP Super) were added to the toluene solution, and the mixture was stirred at RT overnight. The carbon was filtered off and the filter cake was rinsed with 1.5 L Ethyl acetate. The yellowish solution was concentrated to dryness at reduced pressure to yield 2.38 kg of crude wet material. It was dissolved in 1.5 L of isopropyl acetate at 60° C. under stirring, 9 L of preheated heptane (50° C.) were added, and the mixture was stirred at 60° C. The solution was seeded and slowly cooled to RT under stirring. Stirring was continued at room temperature overnight, then the mixture was cooled to 0° C. for 1 hour. The solid was filtered and dried. The yield was 2.1 kg (87% yield, 95.0% ee).

Example 4

Separation of (R)-1-(3-(cyclopropylmethoxy)-4-(difluoromethoxy)phenyl)-2-(3,5-dichloro-1-pyridin-4-yl)ethanol and (S)-1-(3-(cyclopropylmethoxy)-4-(difluoromethoxy)phenyl)-2-(3,5-dichloro-1-pyridin-4-yl)ethanol (intermediates (VIII) and (II), n=0)

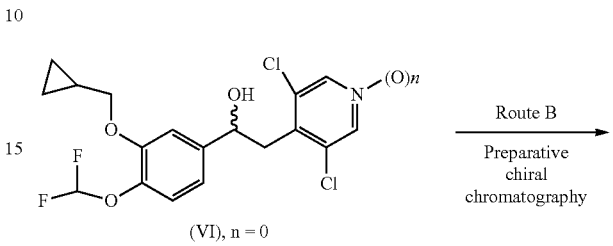

(VI), n = 0

Route B
Preparative chiral chromatography

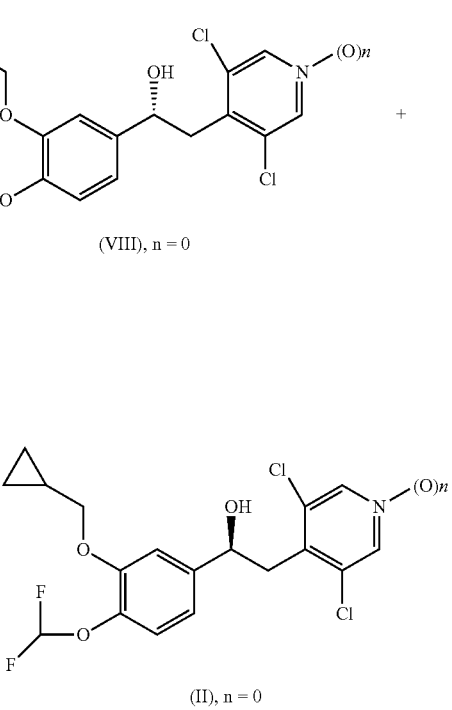

Chromatographic separation was performed on 3000 g of (VI) wherein n is 0, in batch using a Chiralpak IC 20 μm-250*76 mm column and dichloromethane/ethanol 95/5 v/v as mobile phase. A solution of racemic (VI) was loaded in several runs at the top of the chiral column and the eluted fractions of the separated enantiomers collected at the bottom of the column were gathered. (II) Was crystallized from the concentrated DCM/EtOH elution mixture enriched in ethanol. 1440 g (48% yield) of the desired enantiomer (II) wherein n is 0 with HPLC purity >99.5% and HPLC chiral purity >99.5% were obtained. 1470 g (49% yield) of the other enantiomer (VIII) wherein n is 0 with HPLC purity >99% and HPLC chiral purity >99% were also obtained.

Example 4A

Separation of (R)-1-(3-(cyclopropylmethoxy)-4-(difluoromethoxy)phenyl)-2-(3,5-dichloro-1-oxy-pyridin-4-yl)ethanol and (S)-1-(3-(cyclopropyl-methoxy)-4-(difluoromethoxy)phenyl)-2-(3,5-dichloro-1-oxy-pyridin-4-yl)ethanol (intermediates (VIII) and (II), n=1)

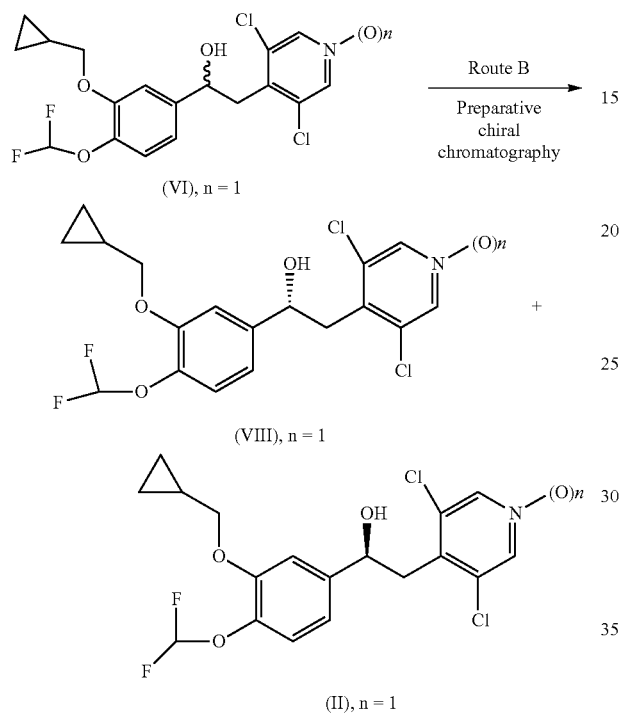

In analogy with Example 4 chromatographic separation using a Chiralpak IC 20 μm-250*76 mm column and methanol as mobile phase can be performed on a solution of racemic (VI) wherein n is 1, to obtain the desired enantiomer (II) wherein n is 1 with high HPLC purity and HPLC chiral purity. The other enantiomer (VIII) wherein n is 1 with high HPLC purity and HPLC chiral purity can also be obtained.

Example 5

Preparation of (S)-3-Cyclopropylmethoxy-4-methane sulfonyl aminobenzoic Acid-1-(3-cyclopropylmethoxy-4-difluoromethoxy-phenyl)-2-(3,5-dichloro-1-pyridin-4-yl)-ethyl ester (compound (I), n=0)

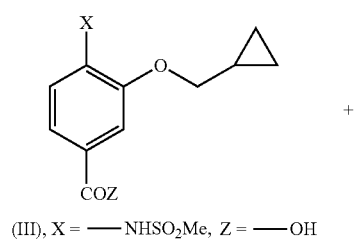

(III), X = —NHSO₂Me, Z = —OH

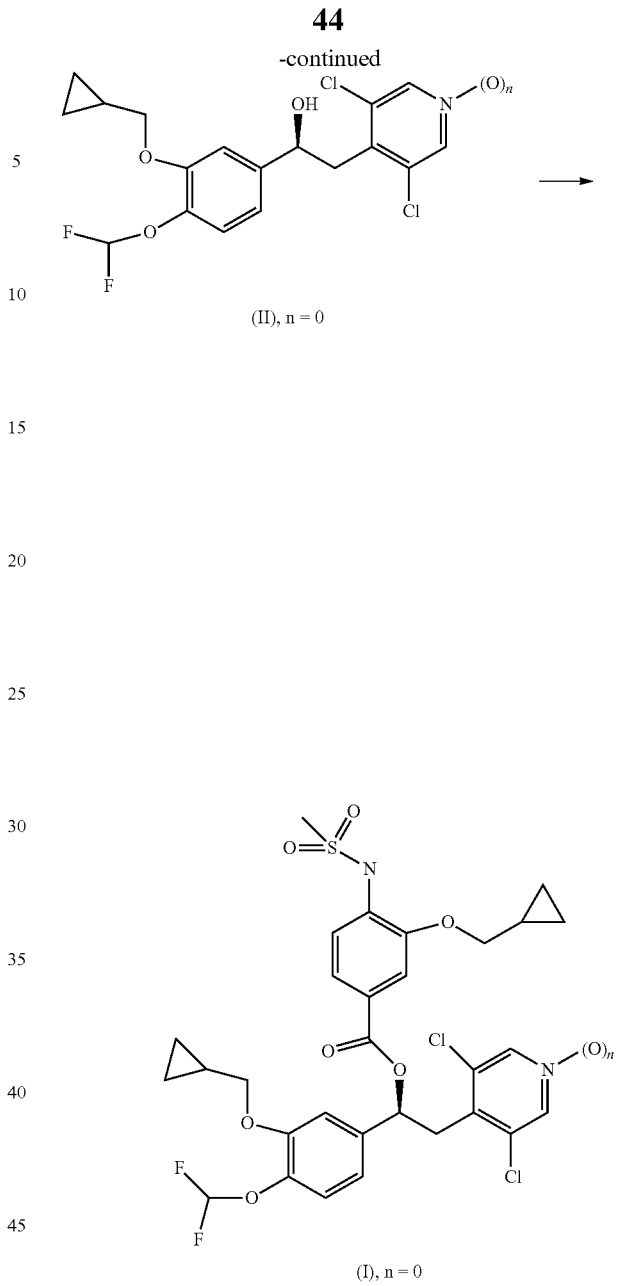

75 g of (III) wherein X is —NHSO₂Me and Z is —OH, were suspended in 750 ml of DCM; 42,5 g of N,N-carbonyldiimidazole were added portion-wise and the obtained solution was stirred at RT for 30 minutes. 375 ml of Toluene were added, followed by 85 g of (II) wherein n is 0 and the mixture was heated up to reflux. DCM was removed by distillation, then the suspension was stirred at 100° C. overnight. The obtained solution was cooled to 40° C., added with 500 ml of Ethyl acetate and washed with NaHCO₃ solution and brine. The product was isolated by crystallization from Ethyl acetate/Heptane, and re-crystallized with the same solvent mixture to obtain a white solid (recovery 129 g, 73% yield).

Product characterization is described in WO 2010089107, which is incorporated herein by reference in its entirety, Example 15.

Example 6

Preparation of (S)-3-Cyclopropylmethoxy-4-methanesulfonylaminobenzoic Acid-1-(3-cyclopropyl-methoxy-4-difluoromethoxy-phenyl)-2-(3,5-dichloro-1-oxy-pyridin-4-yl)-ethyl ester (compound (I), n=1)

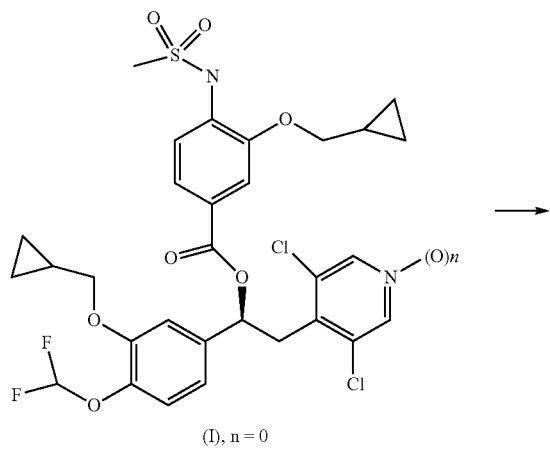

(I), n = 0

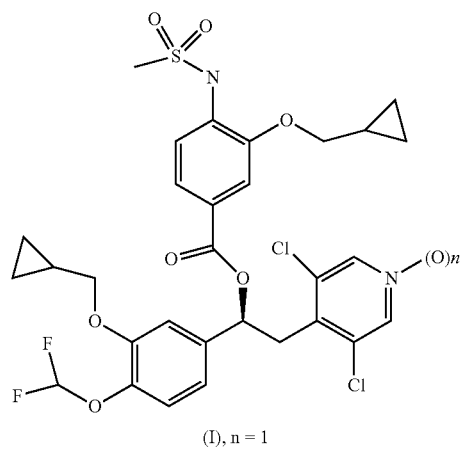

(I), n = 1

Procedure with H$_2$O$_2$/Acetic acid.

73 g of (I) wherein n is 0, were charged in a flask, followed by 150 ml of toluene and 290 ml of acetic acid and 75 ml of 35% H$_2$O$_2$ and the mixture was heated up to 80° C. for 8 hours. The mixture was cooled down to 50° C., 750 ml of ethyl acetate were added, and the aqueous phase removed; the organic phase was washed with water and a 10% NaHCO$_3$ aqueous solution to an alkaline pH, and the solvent was removed by distillation. The crude material was purified by crystallization from 375 ml of ethyl acetate and 225 ml of n-heptane and dried in a static tray drier to obtain a white solid (recovery 65.1 g, 87.1% yield).

Product characterization is described in WO 2010089107 which is incorporated herein by reference in its entirety, Example 17.

Example 7

Preparation of (S)-(3-Cyclopropylmethoxy-4-difluoromethoxyphenyl)-2-(3,5-dichloro-1-oxy-pyridin-4-yl)-ethanol (intermediate (II), n=1)

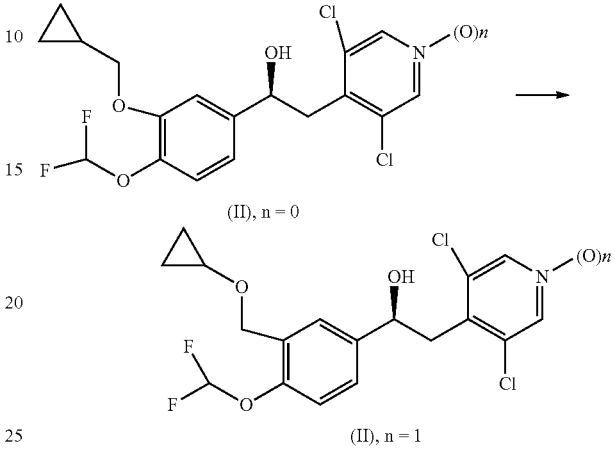

Procedure with H$_2$O$_2$/Acetic acid.

490 g of (II) wherein n is 0, were loaded into a reactor together with 1960 ml of glacial acetic acid. The mixture was heated up to 50° C. then gradually 980 ml of hydrogen peroxide 30 to 35% in water were added and the mixture was kept under stirring at the same temperature for 16 hours. 2000 ml of purified water were slowly added and (II) wherein n=1 precipitated as a solid. The slurry was cooled down to 10° C. and kept under stirring for 3 hours. The solid was then filtered off and the obtained solid was washed with 1000 ml of water. The wet solid (II) wherein n is 1 was re-suspended in 2000 ml of water for 2 hours and in 2000 ml of diisopropyl ether for 3 hours. The wet solid was dried under vacuum. 433 g of white solid were obtained (85% yield).

Product characterization is described in WO 2010089107 which is incorporated herein by reference in its entirety, Example 7.

Procedure with Oxone®.

456 g of Oxone® (KHSO$_5$*½KHSO$_4$*½K$_2$SO$_4$) and 1.2 L of water were added in a reactor and the mixture was stirred at RT. 400 g of (II) wherein n is 0, and 3.2 L of methanol were added and the mixture was heated up to 70° C. for 3 hours. Further 50 g of Oxone® were added and after 1.5 hours, the reaction was completed. The alcohol was distilled off and 4 L of water and 2 L of ethyl acetate were added at 50° C. The aqueous phase was discharged and the organic phase was washed with 800 ml of water and concentrated under vacuum to 1.5 L. 4 L of toluene were added, and the mixture was concentrated under vacuum to 2.5 L while the product precipitation initiated. The suspension was cooled down to 10° C. and kept under stirring for 1.5 hours. The obtained solid was filtered and washed with 800 ml of toluene. Wet solid was dried under vacuum in a static tray drier. 288 g of white solid were obtained (72% yield).

Product characterization is described in WO 2010089107 which is incorporated herein by reference in its entirety, Example 7.

Example 8

Preparation of (S)-3-Cyclopropylmethoxy-4-methanesulfonylaminobenzoic Acid-1-(3-cyclopropylmethoxy-4-difluoromethoxy-phenyl)-2-(3,5-dichloro-1-oxy-pyridin-4-yl)-ethyl ester (compound (I), n=1)

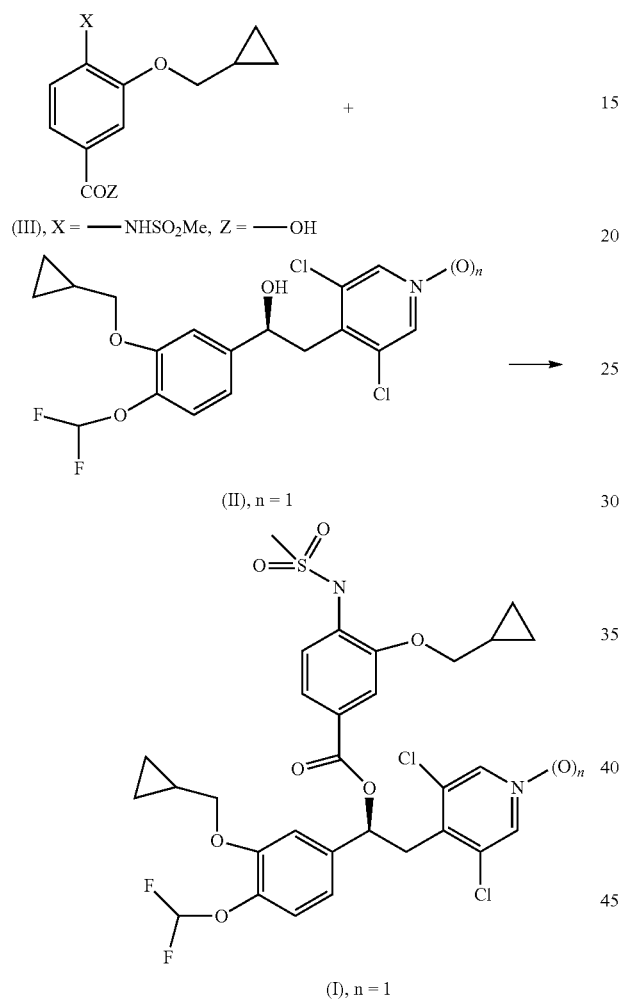

100 g of (III) wherein X is NHSO$_2$Me and Z is —OH and 1 L of ethyl acetate were loaded in a reactor. 57 g of Carbonyldiimidazole were added portion-wise under stirring at 40° C., then the mixture was stirred for 60 minutes. 123 g of (II) wherein n=1 and 3.7 ml of 1,8-Diazabicyclo[5.4.0]undec-7-ene were added, and the mixture was heated up to 75° C. for approximately 4 hours. The organic solution was washed with 500 ml of 1M HCl in water, with 500 ml of 5% NaHCO$_3$ aqueous solution and with 500 ml of 10% NaCl aqueous solution. The organic mixture was heated up to 70° C. under vacuum and concentrated to 600 ml. The mixture was cooled down to 50° C. and 300 ml of n-heptane were added. The solution was seeded, cooled down to 5° C. and kept under stirring for 1.5 hours. The obtained solid was filtered off and dried under vacuum. 168 g of crude solid were obtained (82% yield).

Product characterization is described in WO 2010089107 which is incorporated herein by reference in its entirety, Example 17.

Example 9

Preparation of (S)-3-Cyclopropylmethoxy-4-methanesulfonylamino-benzoic acid 1-(3-cyclopropylmethoxy-4-difluoromethoxy-phenyl)-2-(3,5-dichloro-1-oxy-pyridin-4-yl)-ethyl ester (Compound (I), n is 1)—Solvated from Ethanol A solution of crude compound (I) wherein n is 1 was loaded in a 1L reactor. DCM (90 ml) and EtOH (300 ml) were added, the white suspension was stirred and warmed to reflux until complete dissolution. The DCM was distilled off and a white solid started to precipitate. The ethanolic solution was further concentrated to 6 to 7 volumes distilling off part of the EtOH and then cooled down to 0 to 5° C. and stirred for 120 minutes. The obtained solid was filtered and washed with 30 ml of EtOH. Wet solid was dried under vacuum in a static tray drier. 28.55 g of white solid were obtained (95% yield).

The compound of formula (I) wherein n is 1 obtained as solvate as per Example 9, was investigated to determine the melting point by Differential Scanning calorimetry (DSC), Raman spectroscopy to observe vibrational, rotational and low-frequency modes and the X-ray powder diffraction (XRPD) pattern.

It is characterized by:
a melting range of 87° to 101° C. determined by DSC at a scan rate of 10° C./min.;
a X-ray powder diffraction pattern characterized by the following XRPD peaks (Bruker D8 Advance con Xray Diffraction Tube type KFL CuKα2): 7.45; 7.87; 8.51; 10.12; 10.28; 12.66; 13.29; 13.45; 14.95; 16.14; 16.34; 17.05; 17.74; 18.05; 18.48; 18.88; 19.05; 19.33; 19.85; 20.18; 20.65; 21.3; 22.96; 23.55; 23.87; 24.41; 24.66; 24.88; 25.62; 25.82; 26.45; 28.12 and 28.53±0.2 degrees/2 theta.

Example 10

Crystallization of Compound (I) wherein n is 1—Form A

Procedure from Ethyl Acetate/Heptane 5 g of crude (I) wherein n is 1 were loaded in a reactor together with 30 ml of ethyl acetate and the suspension was stirred while heating to 75° C. until complete dissolution of the solid. 15 ml of n-heptane were added and the solution was allowed to reach RT. The suspension was cooled down to 5° C. for 2 hours, filtered and dried under vacuum. A white solid, the so-called Form A, was obtained (3.6g, 72% yield).

The compound of formula (I) wherein n is 1 obtained as Form A as per Example 10, was investigated to determine the melting point by Differential Scanning calorimetry (DSC), Raman spectroscopy to observe vibrational, rotational and low-frequency modes and the X-ray powder diffraction (XRPD) pattern.

It is characterized by:
a melting range of 144°-147° C. determined by DSC at a scan rate of 10° C./min.;
a X-ray powder diffraction pattern characterized by the following XRPD peaks (Bruker D8 Advance con Xray Diffraction Tube type KFL CuKα2): 7.48; 7.93; 8.55; 10.15; 10.32; 12.72; 13.51; 16.18; 16.46; 17.79; 18.08;

18.53; 18.94; 19.1; 19.89; 20.2; 21.37; 22.96; 23.63; 24.87; 25.82; 26.51; 28.09; and 28.61±0.2 degrees/2 theta.

Procedure from Isopropyl Acetate 5 g of crude (I) wherein n is 1 were loaded in a flask with 20 ml of isopropyl acetate and the suspension was heated to reflux until complete dissolution. The mixture was cooled down to 0° C. and stirred for 2 hours. The obtained solid was filtered and washed with 10 ml of isopropyl acetate. The wet solid was dried under vacuum. 4.05 g of white solid, the crystalline Form A, was obtained (81% yield).

Product characterization is described in WO 2010089107, which is incorporated herein by reference in its entirety, Example

Example 11

Oxidation of intermediate (VII), n=0 to 1-(3-(cyclopropylmethoxy)-4-(difluoromethoxy)phenyl)-2-(3,5-dichloro-1-oxy-pyridin-4-yl)ethanone (intermediate (VII), n=1)

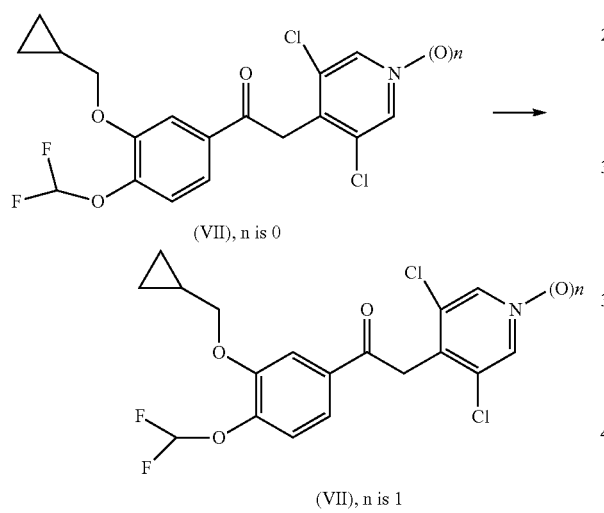

Procedure with H₂O₂/Acetic acid.

0.5 g of (VII) wherein n is 0 were loaded into a 50 ml flask together with 3 ml of glacial acetic acid. The homogeneous solution was heated up to 50° C. then gradually 1 ml of hydrogen peroxide 30 to 35% in water was added, and the mixture was kept under stirring at the same temperature for 21 hours. Then solvent was removed under reduced pressure and the crude solid purified on column chromatography with a gradient elution (Hexane/EtOAc 85/15 to EtOAc 100%), yielding the pure product as a white solid. (yield 50%).

Procedure with Oxone®.

10 g of (VII) wherein n is 0 were loaded into a flask together with 11.44 g of Oxone®, 80 ml of methanol and 30 ml of water. The mixture was heated up to 65° C. for 5 hours and at RT for 48 hours. The alcohol was distilled off and 50 ml of water and 100 ml of toluene were added. The mixture was heated until complete dissolution of the solid, the aqueous phase discharged and the organic phase was concentrated under vacuum to 70 ml. T he suspension was cooled down to 0° C. and kept under stirring for 1.5 hours. The obtained solid was filtered off and dried under vacuum in a static tray drier. 6.7 g of white solid were obtained (60% yield).

Procedure with MCPBA.

0.5 g of (VII) wherein n is 0 were dissolved in 10 ml of THF, 0.34g of MCPBA (3-Chloroperoxybenzoic acid, 77% assay) were added, and the mixture was stirred at RT overnight. HPLC control confirmed almost complete conversion. The solution was partitioned between 100 ml of ethyl acetate and 50 mo of a aqueous 5% solution of potassium hydrogencarbonate. The organic phase was washed with further 50 ml of basic solution and dried under vacuum. The crude was purified on silica pad with a mixture of ethyl acetate and dichloromethane as eluent. 0.22 g of (VII) wherein n=1 were obtained (42% yield).

Example 12

Oxidation of intermediate (VI), n=1 to 1-(3-(cyclopropylmethoxy)-4-(difluoromethoxy)phenyl)-2-(3,5-dichloro-1-oxy-pyridin-4-yl)ethanone (intermediate (VII), n=1)

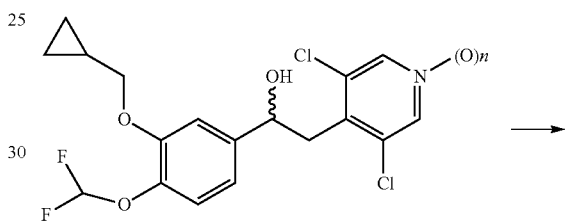

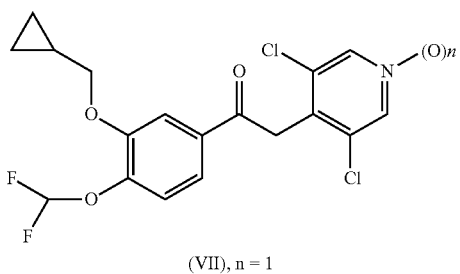

Procedure with DMP.

Alcohol (VI) wherein n is 1 (1.0 g, 2.38 mmol) was suspended in acetone (15 ml). The suspension was cooled under stirring at 0 to 5° C. with an ice-bath. Dess-Martin periodinane (1.4 g, 3.3 mmol) was then added in a single portion. The reaction was initially exothermic and after 1 hour it was left to reach RT. After 20 hours, the reaction went to completion and was quenched with 10 mL of a 10% aq. Sodium metabisulfite solution and 30 mL of 15% potassium carbonate aqueous solution were added. The mixture was stirred at 25° C. for 0.5 hours, and the solid filtered to afford ketone (VII) wherein n is 1 in quantitative yield.

Example 13

Preparation of 3-(cyclopropylmethoxy)-4-nitrobenzoic acid (intermediate (III), X=—NO₂ and Z=—OH)

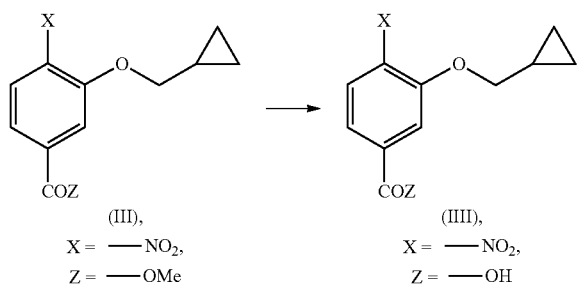

(III) Wherein X is —NO₂ and Z is —OMe was prepared according to the procedure described in WO 2010/089107, which is incorporated herein by reference in its entirety, Example 18. 550 g of (III) wherein X is —NO₂ and Z is —OMe were loaded in a reactor, followed by 1.65 L of THF and 2.85 L of a 1 M aqueous solution of lithium hydroxide. The mixture was heated up to 40° C. for 1.5 hours, then cooled to RT. 4.4 L of ethyl acetate were added, followed by 240 ml of HCl 37% aqueous solution. The aqueous phase was discharged and the organic phase was washed twice with 2.75 L of water and then concentrated under vacuum at 50° C., 1.65 L of n-heptane were added at the same temperature, and the suspension was cooled down to RT. The solid was filtered off and dried in a vacuum tray drier obtaining 337 g of (III) wherein X is —NO₂ and Z is —OH (73% yield).

Example 14

Preparation of (S)-3-Cyclopropylmethoxy-4-nitrobenzoic Acid-1-(3-cyclopropylmethoxy-4-difluoromethoxy-phenyl)-2-(3,5-dichloro-1-pyridin-4-yl)-ethyl ester (intermediate (IV), n=0)

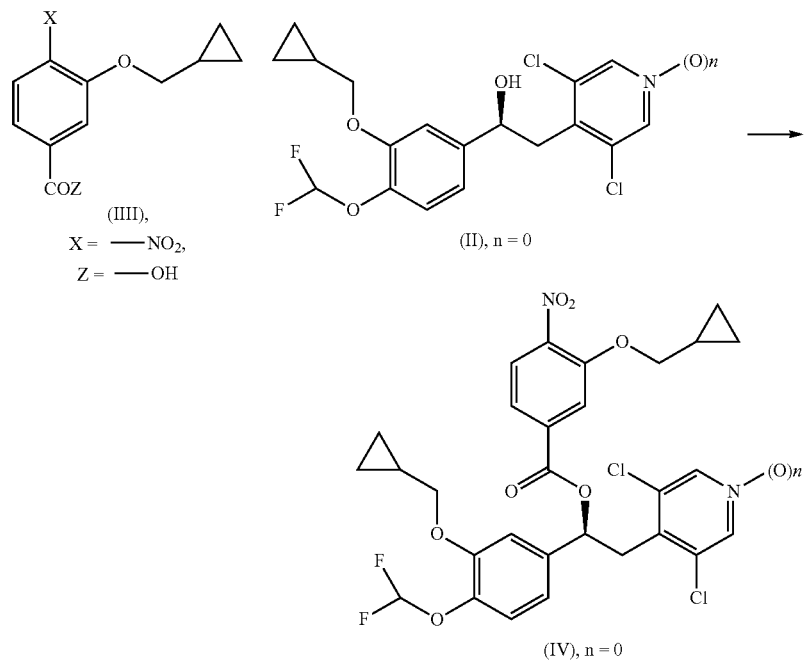

Intermediate (III) wherein X is —NO₂, Z is —OH (80 g, 0.34 mol, ref) and (II) wherein n is 0 (109.1 g, 0.27 mol, 0.9 eq), EDC.HCl (193.9 g, 1.01 mmol, 3 eq), DMAP (20.6 g, 0.17 mol, 0.5 eq) and DMF (400 ml, 5 vol) were mixed together and heated to 75° C. overnight. The solution was partitioned between water and ethyl acetate, the organic phase is washed with acidic and basic aqueous solution and concentrated under vacuum. The crude material was crystallized with EtOH (1200 ml), acetone (100 ml). A white solid was obtained (101 g, 60% yield respect to (VIII)).

$^1$H NMR (400 MHz, DMSO-$d_6$) δ ppm 8.60 (s, 2 H), 7.97 (d, J=8.38 Hz, 1 H), 7.61-7.80 (m, 2 H), 7.18-7.32 (m, 2 H), 7.02-7.14 (m, 2 H), 6.27 (dd, J=9.70, 3.97 Hz, 1 H), 4.04-4.21 (m, 2 H), 3.89-4.02 (m, 2 H), 3.74 (dd, J=14.11, 9.70 Hz, 1 H), 3.45 (dd, J=13.89, 4.19 Hz, 1 H), 1.10-1.30 (m, 2 H), 0.49-0.65 (m, 4 H), 0.36 (qd, J=5.44, 5.29 Hz, 4 H).

Example 15

Preparation of (S)-3-Cyclopropylmethoxy-4-nitrobenzoic Acid-1-(3-cyclopropylmethoxy-4-difluoromethoxy-phenyl)-2-(3,5-dichloro-1-oxy-pyridin-4-yl)-ethyl ester (intermediate (IV), n=1)

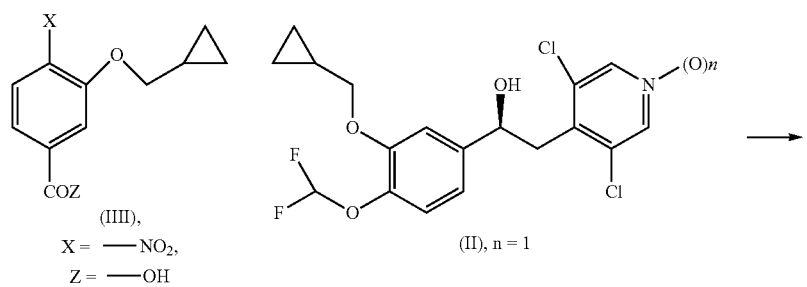

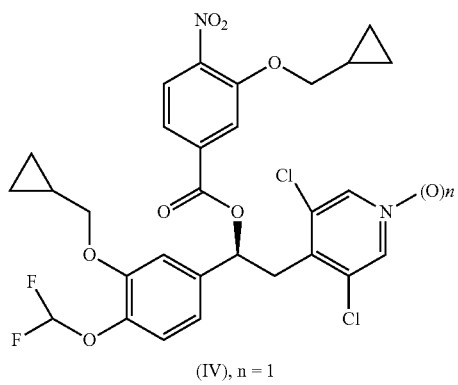

(III) Wherein X is —NO₂ and Z is —OH (80 g, 0.34 mol, ref.), (II) wherein n is 1 (113.9 g, 0.27 mol, 0.9 eq), EDC.HCl (193.9 g, 1.01 mmol, 3 eq), DMAP (20.6 g, 0.17 mol, 0.5 eq) and DMF (400 ml, 5 vol) were mixed together and heated to 100° C. overnight. The solution was partitioned between water and ethyl acetate, the organic phase was washed with acidic and basic aqueous solution and concentrated under vacuum. The crude material was crystallized with EtOH (600 ml), acetone (200 ml) and heptane (200 ml). A white solid was obtained (71 g, 41% yield respect to intermediate (II) wherein is 1).

$^1$H NMR (400 MHz, DMSO-$d_6$) δ ppm 8.56 (s, 2 H), 7.97 (d, J=8.38 Hz, 1 H), 7.62-7.83 (m, 2 H), 7.16-7.32 (m, 2 H), 7.04-7.14 (m, 2 H), 6.20 (dd, J=9.26, 4.41 Hz, 1 H), 4.11 (dd, J=7.06, 3.53 Hz, 2 H), 3.93 (d, J=6.62 Hz, 2 H), 3.62 (d, J=9.26 Hz, 1 H), 3.32 (d, J=9.26 Hz, 1 H), 1.17 — 1.26 (m, 2 H), 0.49-0.67 (m, 4 H), 0.24-0.43 (m, 4 H).

Example 16

Preparation of (S)-3-Cyclopropylmethoxy-4-aminobenzoic Acid-1-(3-cyclopropylmethoxy-4-difluoromethoxy-phenyl)-2-(3,5-dichloro-1-pyridin-4-yl)-ethyl ester (intermediate (V), X=NH₂ and n=0)

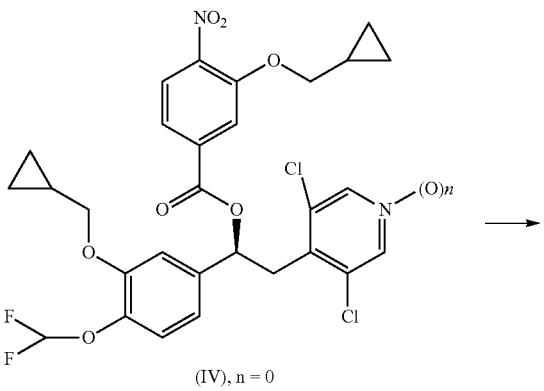

-continued

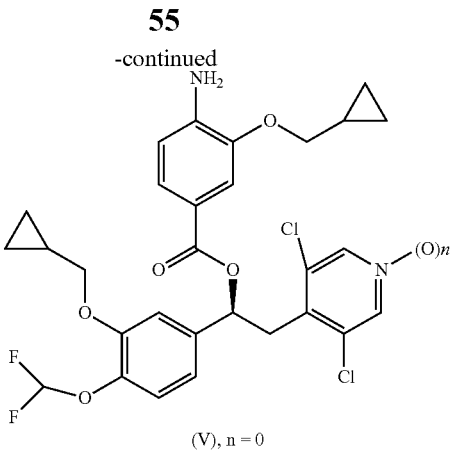

(V), n = 0

Hydrogenation Procedure.

The reactor was charged with 2.5 g of (IV) wherein n is 0, 119 mg of Pd/C catalyst and 25 ml of ethyl acetate. The reactor was then sealed and heated up under mild stirring to the internal temperature of 40° C. The reactor was charged with hydrogen at 4 bars. After 4 hours the conversion was complete. The catalyst was removed by filtration and the solvent distilled under reduced pressure. 2.20 g of product were recovered (90% yield).

$^1$H NMR (400 MHz, CDCl3) δ ppm 8.50 (s, 2 H), 7.49-7.56 (m, 1 H), 7.30-7.36 (m, 2 H), 7.10-7.19 (m, 1 H), 7.00-7.08 (m, 2 H), 6.58-6.68 (m, 1 H), 6.20-6.28 (m, 1 H), 4.11 (bs, 2 H), 3.78-3.92 (m, 4 H), 3.69-3.79 (m, 1 H), 3.30-3.37 (m, 1 H), 1.178-1.32 (m, 2 H), 0.58-0.71 (m, 4 H), 0.28-0.35 (m, 4 H).

Procedure with SnCl$_2$.

2 g of (IV) wherein n is 0 was dissolved in 20 ml of THF and 4.34 g of Tin(II) chloride dihydrate were added. The solution was stirred at 80° C. overnight. The solution was partitioned between 100 ml of ethyl acetate and 100 ml of a 5% aqueous solution of KHCO$_3$. The mixture was filtered to remove the precipitated salts and the aqueous phase was discharged. The organic phase was washed with further KHCO$_3$ and brine. The organic solvent was removed under vacuum isolating (V) wherein n is 0 as a yellow oil (1.84 g, 97% yield).

-continued

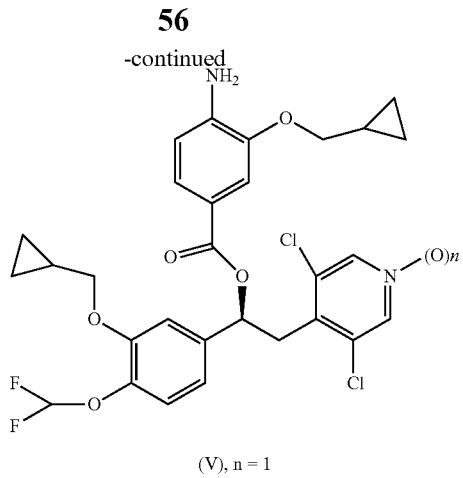

(V), n = 1

Hydrogenation Procedure.

The reactor was charged with 400 mg of (IV) wherein n=1, 8 mg of 1% Pt/C catalyst, and 4 ml of ethyl acetate, sealed and heated up under mild stirring to 60° C., charged with hydrogen at 4 bar and stirring was continued for 4 hours. The mixture was filtered to remove the catalyst and dried under vacuum.

Procedure with SnCl$_2$.

1 g of (IV) wherein n=1 was dissolved in 10 ml of THF and 1.06 g of Tin(II) chloride dihydrate were added. The solution was stirred at RT overnight. The solvent was evaporated under vacuum and 10 ml of ethyl acetate and 10 ml of a 1M aqueous solution of NaOH were added to the crude. The aqueous phase was discharged and the organic phase was washed with 10 ml of a 10% aqueous solution of NaCl. The organic solvent was removed and the crude was suspended in diethyl ether and stirred until a solid was obtained; it was filtered, washed with 4 ml of diethyl ether and dried in a static tray drier. A white solid was obtained (0.68 g, 71.3%).

$^1$H NMR (400 MHz, DMSO-d$_6$) δ ppm 8.55 (s, 2 H), 7.40 (dd, J=8.38, 1.76 Hz, 1 H), 7.28 (d, J=1.76 Hz, 1 H), 7.15-7.21 (m, 2 H), 6.99-7.08 (m, 2 H), 6.64 (d, J=8.38 Hz, 1 H), 6.14 (dd, J=9.59, 4.30 Hz, 1 H), 5.63 (s, 2 H), 3.88-3.96 (m, 2 H), 3.70-3.88 (m, 2 H), 3.55 (dd, J=14.11, 9.92 Hz, 1 H), 3.24-3.31 (m, 1 H), 1.11-1.34 (m, 2 H), 0.47-0.65 (m, 4 H), 0.19-0.41 (m, 4 H).

Example 17

Preparation of (S)-3-Cyclopropylmethoxy-4-aminobenzoic Acid-1-(3-cyclopropylmethoxy-4-difluoromethoxy-phenyl)-2-(3,5-dichloro-1-oxy-pyridin-4-yl)-ethyl ester (intermediate (V), n=1)

Example 18

Preparation of (S)-3-Cyclopropylmethoxy-4-methanesulfonylamino-benzoic acid 1-(3-cyclopropylmethoxy-4-difluoromethoxy-phenyl)-2-(3,5-dichloro-pyridin-4-yl)-ethyl ester (compound (I), n=0)

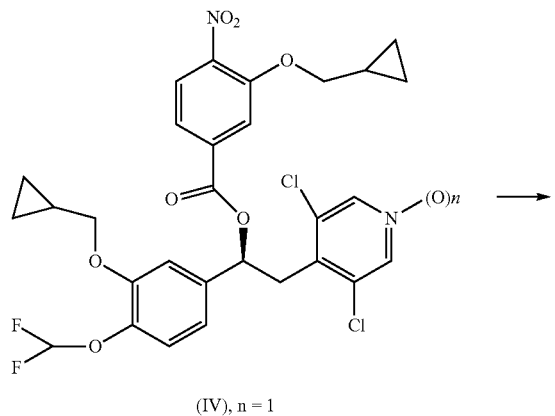

(IV), n = 1

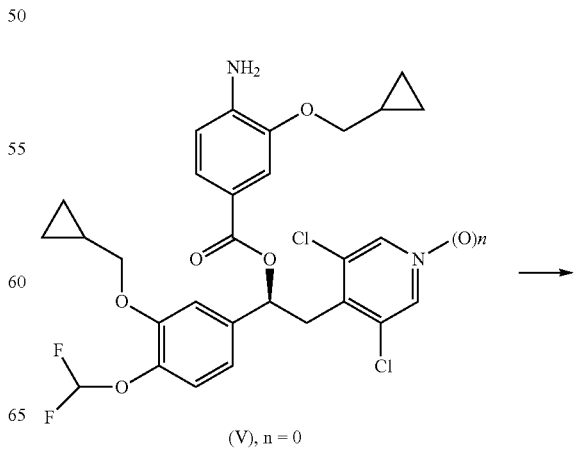

(V), n = 0

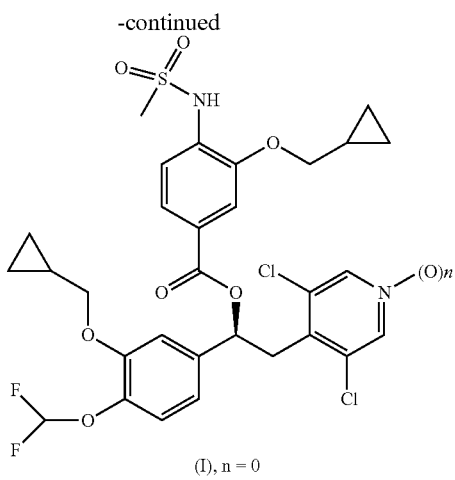

(I), n = 0

0.5 g of (V) wherein n is 0 (0.84 mmol) were dissolved in DCM (7 ml) and TEA (0.17 ml, 1.26 mmol), then methanesulfonyl chloride (0.11 g, 0.93 ml) was slowly added, and the solution stirred at RT for 20 hours. The reaction was then quenched with water (20 ml) and the organic solvent extracted and washed with a NaCl 5% aqueous solution (10 ml). The solvent was removed and the crude purified on column chromatography with a gradient elution (hexane 100% to hexane/EtOAc 60/40), yielding the pure product as a colorless oil (yield 30%).

Example 19

Oxidation of intermediate (IV) wherein n is 0 to obtain (S)-3-Cyclopropylmethoxy-4-nitrobenzoic Acid-1-(3-cyclopropylmethoxy-4-difluoromethoxy-phenyl)-2-(3,5-dichloro-1-oxy-pyridin-4-yl)-ethyl ester (intermediate (IV), n=1)

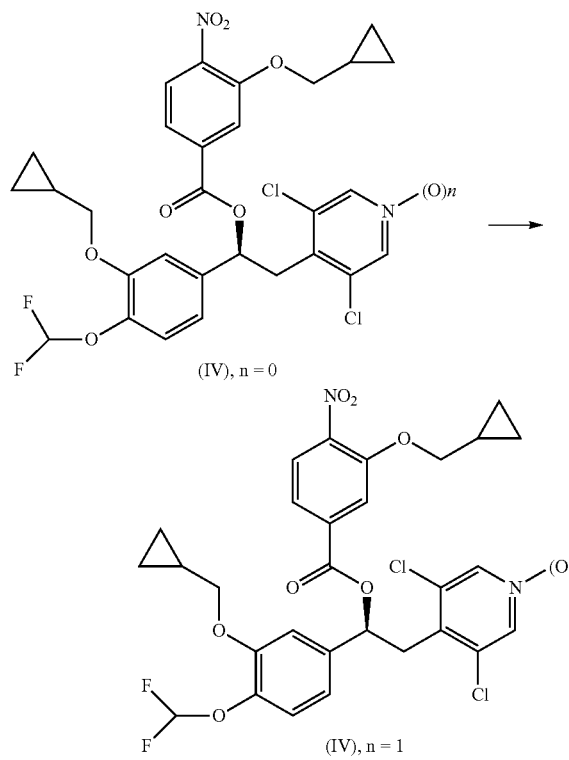

Procedure with H2O2/Acetic Acid.

0.5 g of (IV) wherein n is 0 were loaded into a 50 ml flask with 3 ml of glacial acetic acid. The solution was heated up to 55° C., then gradually 1 ml of hydrogen peroxide (35%) was added and the mixture was kept under stirring at the same temperature for 48 hours. 5 ml of water were added, the product was extracted with ethyl acetate and the organic solvent was removed under reduced pressure yielding the product as a yellow oil (yield 74%).

Procedure with Oxone®.

0.3 g of (IV) wherein n is 0 were charged in a 50 ml flask, followed by 2.4 ml of Methanol, 1 ml of water and 215 mg of Oxone®. The suspension was stirred at 55° C. for 48 hours and at 40° C. for 72 hours. Methanol was removed under reduced pressure and 5 ml of ethyl acetate were added. The aqueous phase was extracted with ethyl Aaetate (3×5 ml), the organic phase was dried under $Na_2SO_4$ and the solvent was removed under reduced pressure yielding the product as a yellowish oil (yield 96%).

Procedure with MCPBA.

0.5 g of (IV) wherein n is 0 were dissolved in 10 ml of THF, 0.22 g of MCPBA (3-chloroperoxybenzoic acid, 77% assay) were added and the mixture was stirred at RT overnight. HPLC control confirmed almost complete conversion. The solution was partitioned between 100 ml of ethyl acetate and 50 ml of an aqueous 5% solution of potassium hydrogencarbonate. Organic phase was washed with further 50 ml of basic solution and dried under vacuum. The crude was purified on silica pad with a mixture of ethyl acetate and dichloromethane as eluent. 0.19 g of (VII) were obtained (37% yield).

Example 20

Methanesulfonylation of (V) wherein n is 1 to obtain (S)-3-Cyclopropylmethoxy-4-methanesulfonylaminobenzoic Acid-1-(3-cyclopropylmethoxy-4-difluoromethoxy-phenyl)-2-(3,5-dichloro-1-oxy-pyridin-4-yl)-ethyl ester (compound (I) wherein n is 1)

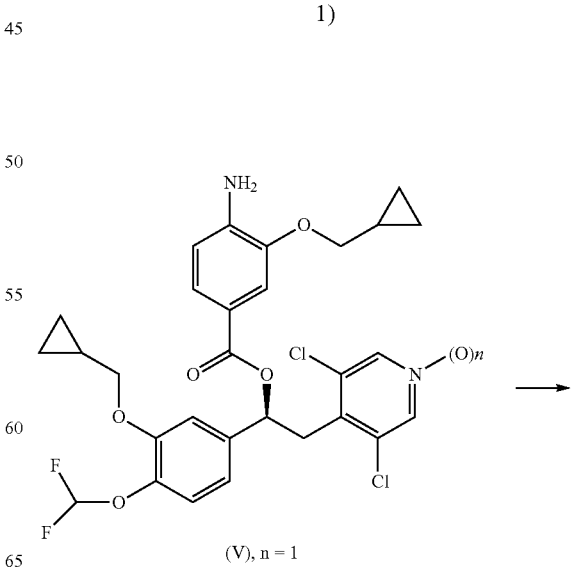

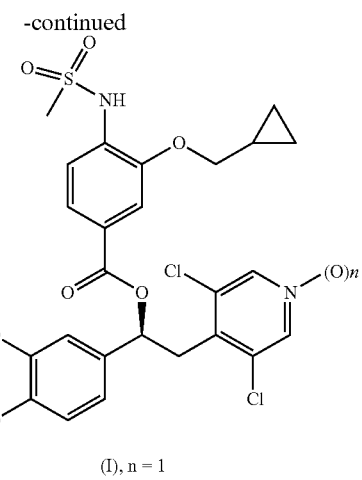

(I), n = 1

0.2 g of (V) wherein n is 1 (0.33 mmol) were dissolved in DCM (3 ml) and TEA (0.05 ml, 0.39 mmol), then methanesulfonyl chloride (0.045 g, 0.07 ml) was slowly added, and solution was stirred at RT for 20 hours. The reaction was then quenched with HCl 1N (10 ml) and the organic solvent extracted and washed with a NaCl 5% aqueous solution (10 ml). The solvent was removed and the crude purified on column chromatography with a gradient elution (Hexane/EtOAc 85/15 to EtOAc 100%), yielding the pure product as a colorless oil (yield 30%).

Example 21

Preparation of 3-hydroxy-4-(difluoromethoxy)-benzoic acid methyl ester

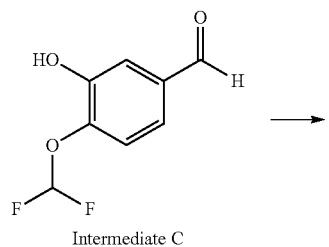
Intermediate C

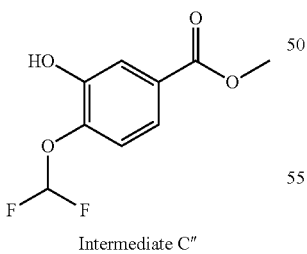
Intermediate C″

100 g of 3-hydroxy-4-(difluoromethoxy)-benzaldehyde (0.53 mol) were dissolved in MeOH (600 ml), solid Oxone® (325 g, 1.06 mol) was added portion-wise in 1 hour and solution was stirred and warmed to 50-55° C. for 2 hours. The solvent was concentrated under vacuum to 200 ml and water (1 L) was added. The resulting heterogeneous solution was stirred at 50 to 55° C., then toluene (500 ml) was added, and the biphasic mixture vigorously stirred. Aqueous phase was discharged and the organic one was washed with water (500 ml). Active charcoal (10 g) was added and the organic solution stirred for 20 minutes. It was filtered on a celite pad, the solvent was concentrated under vacuum to 2 to 3 volumes, and the obtained solution was warmed to 80 to 90° C. n-Heptane (400 ml) was slowly added. The mixture was cooled to 0° C. and the suspension was stirred at 0° C. over-night. The solid was filtered on a Buchner funnel and washed with n-heptane (100 ml). The obtained white solid was dried under vacuum at room temperature. (yield 70%).

Example 22

Preparation of 3-(cyclopropylmethoxy)-4-(difluoromethoxy)-benzoic acid methyl ester

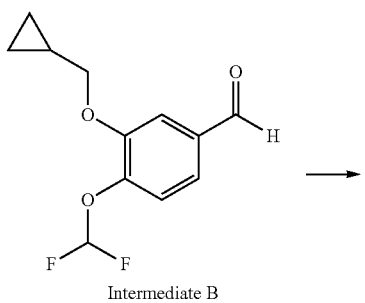
Intermediate B

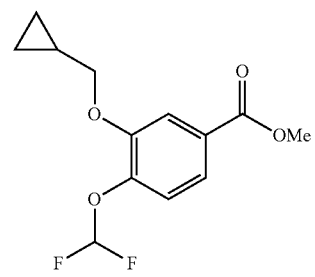
Intermediate B″

873 g of 3-(cyclopropylmethoxy)-4-(difluoromethoxy)-benzaldehyde (3.61 mol) were dissolved in MeOH (4.4 L), then solid Oxone® (1,86 Kg, 6.06 mol) was added portion-wise in 1 hour, and the solution was stirred and warmed to 55 to 60° C. for 2 hours. The solvent was concentrated under vacuum to 1,6 L and water (7 L) was added. The resulting heterogeneous solution was stirred at 50 to 55° C., then toluene (3 L) was added, and the biphasic mixture vigorously stirred. Aqueous phase was discharged and the organic one was washed with water (3 L). The solvent was concentrated under vacuum to 2 to 3 volumes, and the obtained solution warmed to 80 to 90° C. n-Heptane (5,5 L) was slowly added. The mixture was cooled to −10° C., and the suspension was stirred at −10° C. over-night. The solid was filtered on a Buchner funnel and washed with n-heptane (1 L). The obtained yellow solid was dried under vacuum at room temperature. (yield 52%).

Example 23

Preparation of 1-(3-(cyclopropylmethoxy)-4-(difluoromethoxy)phenyl)-2-(3,5-dichloro-1-pyridin-4-yl)ethanone (intermediate (VII), n=0)

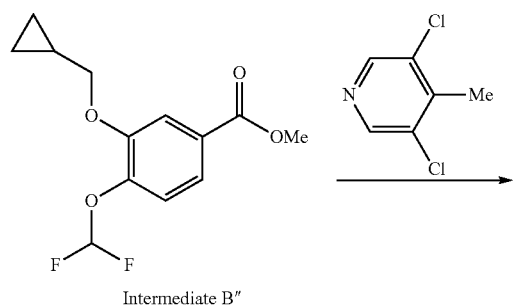

Intermediate B''

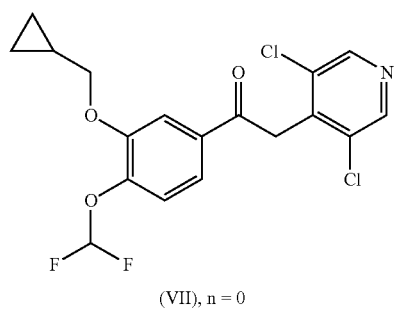

(VII), n = 0

3-(cyclopropylmethoxy)-4-(difluoromethoxy)-benzoic acid methyl ester (30 g, 0.11 mol) and 3,5-dichloro-4-methyl-pyridine (21.4 g, 0.13 mol) were charged in a 1 L reactor and dissolved in THF (120 ml). The homogeneous solution was cooled to −10° C. under stirring. A 1M solution of lithium bis(trimethylsilyl)amide in THF (0.22 mol, 220 ml) was slowly added in 30 minutes. The mixture was stirred at low temperature for 15 to 30 minutes, then quenched with a 10% aqueous solution of HCl (250 ml) and warmed to room temperature. Ethyl acetate (300 ml) was added, and the biphasic mixture vigorously stirred for 15 to 20 minutes. Aqueous phase was re-extracted with ethyl acetate (150 ml). The re-united organic phases were concentrated to 2 volumes.

Isopropanol (240 ml) was added and the solution was concentrated again to 2 to 3 volumes. Isopropanol (150 ml) was added and the solution was cooled to 0° C. obtaining the precipitation of a pale-yellow solid. After 3 hours the solid was filtered on a Buchner funnel and washed with one volume of cold isopropanol. The obtained solid was dried under vacuum at RT. (yield 90.5%).

Example 24

Preparation of 3-(cyclopropylmethoxy)-4-(difluoromethoxy)-benzoic acid methyl ester

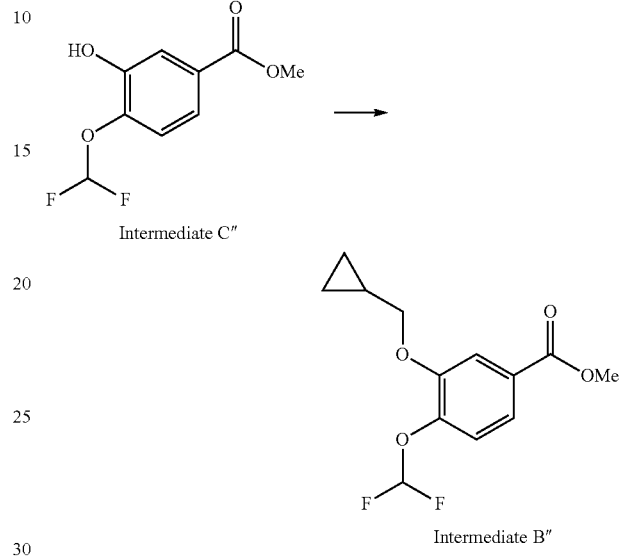

Procedure with DMF and Potassium Carbonate.

3-hydroxy-4-(difluoromethoxy)-benzoic acid methyl ester (5 g, 22.9 mmol), K2CO3 (4.75 g, 34.4 mmol), NaI (0.34 g, 2.3 mmol) and bromo-methylcyclopropane (3.7 g, 27.5 mmol) were dissolved in DMF (25 ml), and the heterogeneous mixture was stirred and warmed at 80° C. for two hours. The suspension was cooled to room temperature, and water (50 ml) was added under stirring. The heterogeneous mixture was cooled to 0 to 5° C. for 60 to 90 minutes, and the solid filtered on a gooch funnel and washed with water (50 ml). An orange solid was obtained. It was dried under vacuum at room temperature. (yield 95.8%).

Example 25

Preparation of 3-(cyclopropylmethoxy)-4-(difluoromethoxy)-benzoic acid methyl ester

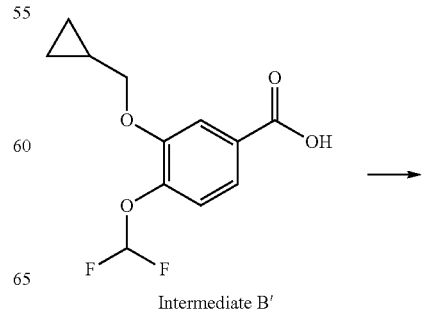

Intermediate B'

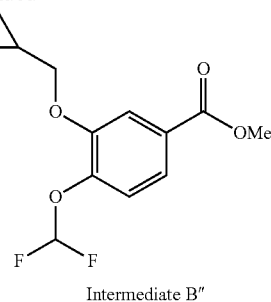

Intermediate B″

Procedure with DMA, Potassium Carbonate and MeI.

3-(cyclopropylmethoxy)-4-(difluoromethoxy)-benzoic acid (50 g, 193.6 mmol), and K2CO3 (28.1 g, 203.3 mmol), were suspended in DMA (400 ml), and the suspension was warmed to 75 to 85° C. A solution of MeI (32.97 gr, 232.0 mmol) in DMA (100 ml) was added through a dropping funnel in 1 hour. At the end of addition the suspension was cooled to 0 to 5° C., and water (500 ml) was added under stirring. The precipitation of a white solid occurred. The heterogeneous cold mixture was stirred for 60 to 90 minutes, and the solid filtered on a gooch funnel and washed with water (50 ml). Product was obtained as a white solid. It was dried under vacuum at room temperature. (yield 98.1%).

Example 26

Preparation of 3-hydroxy-4-(difluoromethoxy)-benzoic acid methyl ester

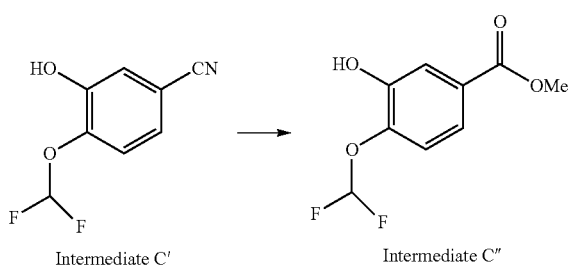 [SMILES: N#Cc1ccc(OC(F)F)c(O)c1 ; COC(=O)c1ccc(OC(F)F)c(O)c1]

Intermediate C'  Intermediate C″

In a 50 ml flask 3-(cyclopropylmethoxy)-4-(difluoromethoxy)-benzonitrile (0.5 g, 2.7 mmol), was dissolved in MeOH (3 ml), and the homogeneous solution was stirred at room temperature. 91% Aqueous H2SO4 (1 ml) was slowly added drop wise and the solution was warmed at 50° C. for a week. The solution was cooled to 0 to 5° C., and water (10 ml) was added, and the obtained suspension was stirred at low temperature for 1 hour.

The suspension was filtered on a gooch funnel. The product was obtained as a white solid (yield 78%).

Example 27

Preparation of (R/S)-1-(3-(cyclopropylmethoxy)-4-(difluoromethoxy)phenyl)-2-(3,5-dichloro-1-oxy-pyridin-4-yl)ethanol (intermediate (VI), n=1)

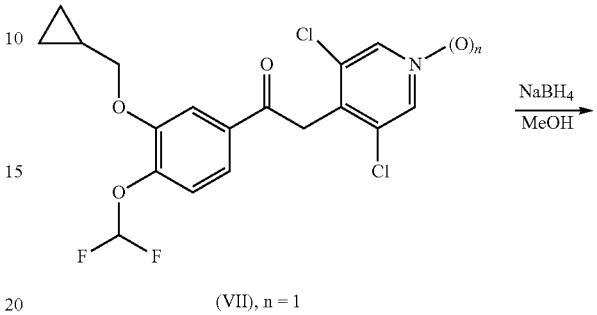

In a 100 ml round bottomed flask (VII) wherein n is 1 (0.2 g, 0.48 mmol) was added under nitrogen atmosphere, suspended in MeOH (10 ml) and cooled to 0 to 5° C. NaBH4 (18.0 mg, 0.48 mmol) was added, and the suspension was stirred for 1.5 hours. The reaction was quenched with H2O (25 ml) and warmed to room temperature. The aqueous solution was extracted twice with ethyl acetate (2×15 ml), and the re-united organic phases were dried over Na2SO4. The solvent was evaporated under reduced pressure obtaining a crude solid. It was dissolved in hot toluene (10 ml, 85-90° C.) and crystallized by cooling the solution to 0 to 5° C. for 2 hours. The obtained solid was filtered, washed with 10 ml of toluene and dried under vacuum in a static tray drier. 164.5 mg of white solid were obtained. (81.6% yield).

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical formulation, comprising:
(A) a crystal form of a compound of formula (I):

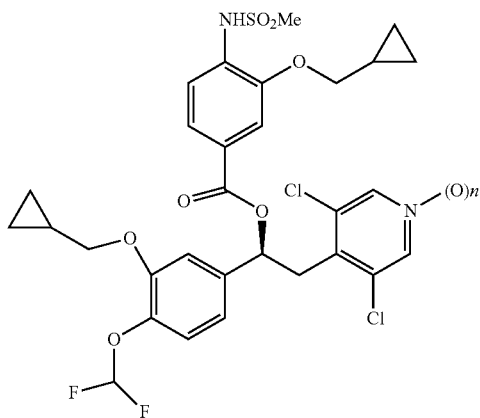

wherein:
n is 1; and
said crystal form of a compound of formula (I) exhibits the following characteristic XRPD peaks: 7.48; 7.93; 10.15; 10.32; 12.72; 13.51; 16.18; 16.46; 18.08; 18.53; 18.94; 8.55; 17.79; 19.89; 19.1; 20.2; 21.37; 22.96; 23.63; 24.87; 26.51; 28.09; 28.61 and 25.82±0.2 degrees/2 theta (CuKα2); and
(B) a pharmaceutically acceptable carrier.

2. The pharmaceutical formulation according to claim 1, which is in a form suitable for inhalation or intranasal administration.

3. The pharmaceutical formulation according to claim 1, which is in a dosage form of a capsule.

4. The pharmaceutical formulation according to claim 1, which is in a form of a dry powder suitable for inhalation.

5. A method for treating an inflammatory or obstructive respiratory disease, comprising administering to a subject in need thereof an effective amount of a pharmaceutical formulation according to claim 1.

6. A method for treating asthma or chronic obstructive pulmonary disease, comprising administering to a subject in need thereof an effective amount of a pharmaceutical formulation according to claim 1.

7. A process for preparing a crystal form of a compound of formula (I):

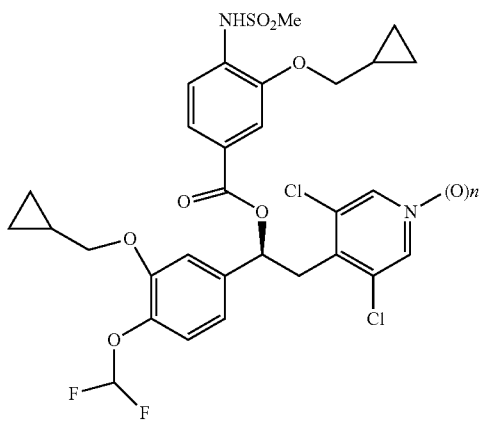

wherein:
n is 1; and
said crystal form of a compound of formula (I) exhibits the following characteristic XRPD peaks: 7.48; 7.93; 10.15; 10.32; 12.72; 13.51; 16.18; 16.46; 18.08; 18.53; 18.94; 8.55; 17.79; 19.89; 19.1; 20.2; 2.37; 22.96; 23.63; 24.87; 26.51; 28.09; 28.61 and 25.82±0.2 degrees/2 theta degrees/2 theta (CuKα2),
wherein said process comprises heating a suspension of compound of formula (I) to a temperature of 50 to 90° C. to obtain a solution, cooling said solution to a temperature of 0 to 5° C. for a time of 1 to 5 hours, to obtain crystals.

8. The process according to claim 7, further comprising filtering and washing said crystals.

9. The process according to claim 7, wherein the total amount of impurities in the crystal form of the compound of formula (I) is less than 5% w/w.

10. The process according to claim 7, wherein the total amount of impurities in the crystal form of the compound of formula (I) is less than 2.5% w/w.

11. The process according to claim 7, wherein the total amount of impurities in the crystal form of the compound of formula (I) is less than 1% w/w.

12. The process according to claim 7, wherein the total amount of impurities in the crystal form of the compound of formula (I) is less than 0.5% w/w.

13. The process according to claim 7, wherein the percentage of crystallinity in said crystal form of the compound of formula (I) is equal to or higher than 90% w/w.

14. The process according to claim 13, wherein the percentage of crystallinity is higher than 95% w/w.

15. The process according to claim 7, which comprises heating a suspension of said compound of formula (I) in ethyl acetate/heptane or isopropyl acetate.

16. The process according to claim 7, which comprises heating a suspension of a compound of formula (I) together with ethyl acetate to 75° C., adding n-heptane, and cooling to 5° C. for 2 hrs.

17. The process according to claim 7, which comprises heating a suspension of a compound of formula (I) together with isopropyl acetate to reflux until complete dissolution, cooling to 0° C. and stirring for 2 hrs.

18. A crystal form of a compound of formula (I) obtained according to the process of claim 7.

19. A method for the treatment of an inflammatory or obstructive respiratory disease, comprising administering to a subject in need thereof an effective amount of a crystal for according to claim 18.

20. A method according to claim 19, wherein said inflammatory or obstructive respiratory disease is asthma or chronic obstructive pulmonary disease.

* * * * *